(12) United States Patent
Egusa et al.

(10) Patent No.: US 10,603,292 B2
(45) Date of Patent: Mar. 31, 2020

(54) PHARMACEUTICAL COMPOSITION AND PHARMACEUTICAL DOSAGE FORM COMPRISING (E)-4-(2-(AMINOMETHYL)-3-FLUOROALLYLOXY)-N-TERT-BUTYLBENZAMIDE, PROCESS FOR THEIR PREPARATION, METHODS FOR TREATING AND USES THEREOF

(71) Applicant: Boehringer Ingelheim International GmbH, Ingelheim am Rhein (DE)

(72) Inventors: Kenji Egusa, Ikeda (JP); Takuma Katayama, Kobe (JP); Kazutoshi Yokoyama, Osaka (JP); Remko Alexander Bakker, Biberach an der Riss (DE); Ngai Hang Victor Chong, Heidesheim (DE); Joerg Rippmann, Schemmerhofen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/992,262

(22) Filed: May 30, 2018

(65) Prior Publication Data
US 2018/0344672 A1 Dec. 6, 2018

Related U.S. Application Data

(60) Provisional application No. 62/512,896, filed on May 31, 2017, provisional application No. 62/536,002, filed on Jul. 24, 2017.

(51) Int. Cl.
| | |
|---|---|
| A61K 31/166 | (2006.01) |
| A61K 9/20 | (2006.01) |
| A61P 1/16 | (2006.01) |
| A61P 27/02 | (2006.01) |
| A61P 35/00 | (2006.01) |
| A61P 3/00 | (2006.01) |
| A61P 29/00 | (2006.01) |
| A61K 9/28 | (2006.01) |

(52) U.S. Cl.
CPC .......... *A61K 31/166* (2013.01); *A61K 9/2013* (2013.01); *A61K 9/2018* (2013.01); *A61K 9/2059* (2013.01); *A61P 1/16* (2018.01); *A61P 3/00* (2018.01); *A61P 27/02* (2018.01); *A61P 29/00* (2018.01); *A61P 35/00* (2018.01); *A61K 9/2095* (2013.01); *A61K 9/28* (2013.01)

(58) Field of Classification Search
CPC .................................................... A61K 31/166
USPC ....................................................... 514/620
See application file for complete search history.

(56) References Cited

U.S. PATENT DOCUMENTS 9,302,986 B2 * 4/2016 Deodhar ............... C07C 235/46

FOREIGN PATENT DOCUMENTS

| EP | 468929 A2 | 1/1992 |
|---|---|---|
| EP | 2844637 A1 | 3/2015 |
| WO | 2006070930 A1 | 7/2006 |
| WO | 2009121945 A2 | 10/2009 |
| WO | 2010013823 A2 | 2/2010 |
| WO | 2012106303 A1 | 8/2012 |
| WO | 2013163675 A1 | 11/2013 |
| WO | 2017098236 A1 | 6/2017 |

OTHER PUBLICATIONS

International Search Report and Written Opinion for PCT/EP2018064135 dated Jul. 16, 2018.

* cited by examiner

*Primary Examiner* — Kevin E Weddington
(74) *Attorney, Agent, or Firm* — David L. Kershner

(57) ABSTRACT

The present invention relates to pharmaceutical compositions comprising (E)-4-(2-(aminomethyl)-3-fluoroallyloxy)-N-tert-butylbenzamide having the following chemical structure

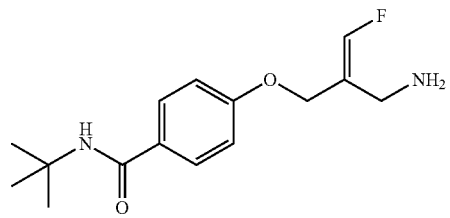

or a pharmaceutically acceptable salt thereof as active pharmaceutical ingredient, particularly to pharmaceutical compositions comprising (E)-4-(2-(aminomethyl)-3-fluoroallyloxy)-N-tert-butylbenzamide hydrochloride, to pharmaceutical dosage forms, to their preparation, their use and methods for therapeutic treatment.

13 Claims, 3 Drawing Sheets

PHARMACEUTICAL COMPOSITION AND PHARMACEUTICAL DOSAGE FORM COMPRISING (E)-4-(2-(AMINOMETHYL)-3-FLUOROALLYLOXY)-N-TERT-BUTYLBENZAMIDE, PROCESS FOR THEIR PREPARATION, METHODS FOR TREATING AND USES THEREOF

TECHNICAL FIELD OF THE INVENTION

The present invention relates to pharmaceutical compositions comprising (E)-4-(2-(aminomethyl)-3-fluoroallyloxy)-N-tert-butylbenzamide having the following chemical structure

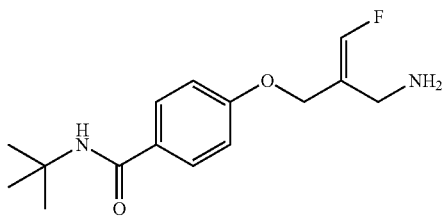 [SMILES: CC(C)(C)NC(=O)c1ccc(OC/C(=C/F)CN)cc1]

or a pharmaceutically acceptable salt thereof as active pharmaceutical ingredient, particularly to pharmaceutical compositions comprising (E)-4-(2-(aminomethyl)-3-fluoroallyloxy)-N-tert-butylbenzamide hydrochloride, and one or more stabilizers. Furthermore, the present invention relates to a pharmaceutical dosage form comprising such a pharmaceutical composition. In addition, the invention relates to a process for the preparation of such a pharmaceutical dosage form. In addition the invention relates to a method for preventing, slowing the progression of, delaying or treating of one or more fibrotic diseases, metabolic diseases, inflammatory diseases, ocular diseases, neuroinflammatory diseases or cancers in a patient in need thereof characterized in that the pharmaceutical composition or pharmaceutical dosage form is administered to the patient. In addition the invention relates to uses of the pharmaceutical composition or dosage form in a method for preventing, slowing the progression of, delaying or treating of one or more diseases as described hereinbefore or hereinafter. Furthermore the present invention relates to methods for treating of non-alcoholic fatty liver disease (NAFLD), non-alcoholic steatohepatitis (NASH) or diabetic retinopathy.

BACKGROUND OF THE INVENTION (E)-4-(2-(Aminomethyl)-3-fluoroallyloxy)-N-tert-butylbenzamide is an amine oxidase, copper containing 3 (AOC3) inhibitor, which is known from WO 2013/163675 (compound 23). Its synthesis and uses thereof are also described in said International Application.

As a precondition for a broadly based use of (E)-4-(2-(aminomethyl)-3-fluoroallyloxy)-N-tert-butylbenzamide and its pharmaceutically acceptable salts in the treatment of the above-mentioned diseases and conditions, a pharmaceutical composition and/or a pharmaceutical dosage form comprising said active ingredients that fulfills the usual criteria needs to be provided. The usual criteria for pharmaceutical compositions include i.a. a good and reproducible bioavailability of the active ingredient, an acceptable form and size, an acceptable shelf-life and a good storage stability, i.e. a low degradation of the active ingredient over time. E.g., one of the acceptance criteria for degradation is a total degradation of not more than 3.0% total degradation after a storage of 36 months, preferably, the total degradation is not more than 1.5% after 36 months of storage or even lower.

Presently, there is an unmet medical need for methods, medicaments and pharmaceutical compositions with a good efficacy with regard to fibrotic diseases, metabolic diseases and ocular diseases, for example non-alcoholic fatty liver (NAFL) disease, non-alcoholic steatohepatitis (NASH) or diabetic retinopathy, while at the same time complying with the standard criteria for pharmaceutical compositions and dosage forms.

AIM OF THE PRESENT INVENTION

The aim of the present invention is to provide a pharmaceutical composition comprising (E)-4-(2-(aminomethyl)-3-fluoroallyloxy)-N-tert-butylbenzamide having the chemical structure shown above or a pharmaceutically acceptable salt thereof, particularly to a pharmaceutical composition comprising (E)-4-(2-(aminomethyl)-3-fluoroallyloxy)-N-tert-butylbenzamide hydrochloride, with an acceptable storage stability.

Another aim of the present invention is to provide a pharmaceutical composition comprising (E)-4-(2-(aminomethyl)-3-fluoroallyloxy)-N-tert-butylbenzamide having the chemical structure shown above or a pharmaceutically acceptable salt thereof, particularly to a pharmaceutical composition comprising (E)-4-(2-(aminomethyl)-3-fluoroallyloxy)-N-tert-butylbenzamide hydrochloride, said pharmaceutical composition showing a reduced formation of degradation products and/or a reduced degradation rate of the active ingredient over time during storage.

Another aim of the present invention is to provide a pharmaceutical composition comprising (E)-4-(2-(aminomethyl)-3-fluoroallyloxy)-N-tert-butylbenzamide having the chemical structure shown above or a pharmaceutically acceptable salt thereof, particularly to a pharmaceutical composition comprising (E)-4-(2-(aminomethyl)-3-fluoroallyloxy)-N-tert-butylbenzamide hydrochloride, having a longer shelf-life.

Another aim of the present invention is to provide a pharmaceutical composition comprising (E)-4-(2-(aminomethyl)-3-fluoroallyloxy)-N-tert-butylbenzamide having the chemical structure shown above or a pharmaceutically acceptable salt thereof, particularly to a pharmaceutical composition comprising (E)-4-(2-(aminomethyl)-3-fluoroallyloxy)-N-tert-butylbenzamide hydrochloride, which avoids or reduces the need of special storage conditions such as e.g. cooling.

Another aim of the invention is to provide a pharmaceutical dosage form comprising (E)-4-(2-(aminomethyl)-3-fluoroallyloxy)-N-tert-butylbenzamide having the chemical structure shown above or a pharmaceutically acceptable salt thereof, particularly to a pharmaceutical dosage form comprising (E)-4-(2-(aminomethyl)-3-fluoroallyloxy)-N-tert-butylbenzamide hydrochloride, which has a short disintegration time, which has good dissolution properties and/or which enables a high bioavailability of the active ingredient in the patient.

Another aim of the invention is to provide a pharmaceutical composition comprising (E)-4-(2-(aminomethyl)-3-fluoroallyloxy)-N-tert-butylbenzamide having the chemical structure shown above or a pharmaceutically acceptable salt thereof, particularly to a pharmaceutical composition comprising (E)-4-(2-(aminomethyl)-3-fluoroallyloxy)-N-tert-butylbenzamide hydrochloride, which has high content uniformity and/or which allows an effective production with regard to time and costs of pharmaceutical dosage forms containing said pharmaceutical composition.

Another aim of the invention it to provide a pharmaceutical composition and a pharmaceutical dosage form, each comprising (E)-4-(2-(aminomethyl)-3-fluoroallyloxy)-N-tert-butylbenzamide having the chemical structure shown above or a pharmaceutically acceptable salt thereof, particularly to a pharmaceutical composition and a pharmaceutical dosage form comprising (E)-4-(2-(aminomethyl)-3-fluoroallyloxy)-N-tert-butylbenzamide hydrochloride, for use in a method for preventing, slowing the progression of, delaying or treating of one or more fibrotic diseases, metabolic diseases, inflammatory diseases, ocular diseases, neuroinflammatory diseases or cancers.

A further aim of the present invention is to provide a method for preventing, slowing the progression of, delaying or treating of one or more fibrotic diseases, metabolic diseases, inflammatory diseases, ocular diseases, neuroinflammatory diseases or cancers in a patient in need thereof.

Another aim of the present invention is to provide a pharmaceutical composition and a pharmaceutical dosage form, each comprising (E)-4-(2-(aminomethyl)-3-fluoroallyloxy)-N-tert-butylbenzamide having the chemical structure shown above or a pharmaceutically acceptable salt thereof, particularly to a pharmaceutical composition and a pharmaceutical dosage form comprising (E)-4-(2-(aminomethyl)-3-fluoroallyloxy)-N-tert-butylbenzamide hydrochloride, with a high efficacy for preventing, slowing the progression of, delaying or treating of one or more fibrotic diseases, metabolic diseases, inflammatory diseases, ocular diseases, neuroinflammatory diseases or cancers, which has good to very good pharmacological and/or pharmacokinetic and/or physicochemical properties.

Another aim of the present invention is to provide a process for the preparation of a pharmaceutical composition and a pharmaceutical dosage form according to the invention which is effective in costs and/or time.

Further aims of the present invention become apparent to the one skilled in the art by description hereinbefore and in the following and by the examples.

SUMMARY OF THE INVENTION

Firstly, conventional pharmaceutical compositions comprising (E)-4-(2-(aminomethyl)-3-fluoroallyloxy)-N-tert-butylbenzamide hydrochloride as the active ingredient, and mannitol and magnesium stearate as filler and lubricant were prepared. However, these pharmaceutical compositions turned out to have an unsatisfactory stability profile, so that they needed to be stored below 8° C., i.e. in the refrigerator, to have a satisfactory shelf life of more than 12 months (cf. table in Example A).

Surprisingly, it was then found out that pharmaceutical compositions comprising (E)-4-(2-(aminomethyl)-3-fluoroallyloxy)-N-tert-butylbenzamide having the following chemical structure

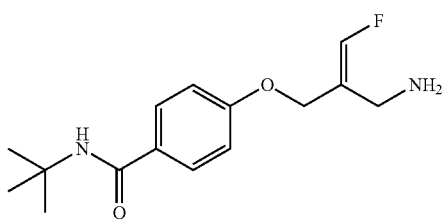 [SMILES: CC(C)(C)NC(=O)c1ccc(OC/C(=C/F)CN)cc1]

or a pharmaceutically acceptable salt thereof as active pharmaceutical ingredient, particularly to pharmaceutical compositions comprising (E)-4-(2-(aminomethyl)-3-fluoroallyloxy)-N-tert-butylbenzamide hydrochloride, and additionally comprising one or more, preferably one stabilizer have a significantly improved stability against degradation of the active ingredient during storage. Thus, a satisfactory shelf-life is achieved even at room temperature (i.e. without cooling).

In one aspect the present invention provides a pharmaceutical composition comprising (E)-4-(2-(aminomethyl)-3-fluoroallyloxy)-N-tert-butylbenzamide having the following chemical structure

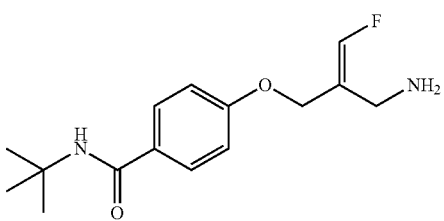 [SMILES: CC(C)(C)NC(=O)c1ccc(OC/C(=C/F)CN)cc1]

or a pharmaceutically acceptable salt thereof as an active pharmaceutical ingredient, and one or more stabilizers.

In a further aspect the present invention provides a pharmaceutical dosage form, preferably a solid pharmaceutical dosage form, for example a tablet, comprising a pharmaceutical composition according to the present invention.

In an embodiment, effervescent preparations including e.g. effervescent granules or powders are excluded from the pharmaceutical compositions and pharmaceutical dosage forms according to the invention.

In another embodiment, pharmaceutical compositions and pharmaceutical dosage forms additionally comprising a source of carbon dioxide e.g. sodium bicarbonate or sodium carbonate are excluded from the invention.

In another aspect the present invention provides a method for preventing, slowing the progression of, delaying or treating of one or more fibrotic diseases, metabolic diseases, inflammatory diseases, ocular diseases, neuroinflammatory diseases or cancers in a patient in need thereof characterized in that a pharmaceutical composition or a pharmaceutical dosage form as described hereinbefore and hereinafter is administered to the patient.

In another aspect the present invention provides methods for treating of non-alcoholic fatty liver disease (NAFLD), non-alcoholic steatohepatitis (NASH) or diabetic retinopathy characterized in that a pharmaceutical composition or a pharmaceutical dosage form comprising (E)-4-(2-(aminomethyl)-3-fluoroallyloxy)-N-tert-butylbenzamide or a pharmaceutically acceptable salt thereof as an active pharmaceutical ingredient (API), in particular a pharmaceutical composition or a pharmaceutical dosage form as described hereinbefore and hereinafter is administered to the patient.

In a further aspect the present invention provides a use of a pharmaceutical composition or a pharmaceutical dosage form comprising (E)-4-(2-(aminomethyl)-3-fluoroallyloxy)-N-tert-butylbenzamide or a pharmaceutically acceptable salt thereof as an active pharmaceutical ingredient (API), in particular a pharmaceutical composition or a pharmaceutical dosage form as described hereinbefore and hereinafter for a method as described hereinbefore and hereinafter.

In another aspect the present invention provides a pharmaceutical composition or a pharmaceutical dosage form comprising (E)-4-(2-(aminomethyl)-3-fluoroallyloxy)-N-tert-butylbenzamide or a pharmaceutically acceptable salt thereof as an active pharmaceutical ingredient (API), in particular a pharmaceutical composition or a pharmaceutical dosage form as described hereinbefore and hereinafter for use in a method as described hereinbefore and hereinafter.

In a further aspect the present invention provides a use of a pharmaceutical composition or a pharmaceutical dosage form comprising (E)-4-(2-(aminomethyl)-3-fluoroallyloxy)-N-tert-butylbenzamide or a pharmaceutically acceptable salt thereof as an active pharmaceutical ingredient (API), in particular a pharmaceutical composition or a pharmaceutical dosage form as described hereinbefore and hereinafter for the manufacture of a medicament for use in a method as described hereinbefore and hereinafter.

In a further aspect the present invention provides a process for making a pharmaceutical composition as described hereinbefore and hereinafter, for example by dry granulation or by direct compression.

In another aspect the present invention provides a pharmaceutical composition obtainable or obtained by a process for making as described hereinbefore and hereinafter.

Further aspects of the present invention become apparent to the one skilled in the art by description hereinbefore and in the following and by the examples.

Definitions

The term "active ingredient" of a pharmaceutical composition according to the present invention means (E)-4-(2-(aminomethyl)-3-fluoroallyloxy)-N-tert-butylbenzamide having the following chemical structure

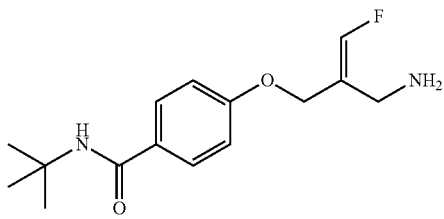 [SMILES: CC(C)(C)NC(=O)c1ccc(OC/C(=C/F)CN)cc1]

or a pharmaceutically acceptable salt thereof, particularly (E)-4-(2-(aminomethyl)-3-fluoroallyloxy)-N-tert-butylbenzamide hydrochloride. Preferably, a crystalline form, such as "Form I", of the active ingredient, in particular of (E)-4-(2-(aminomethyl)-3-fluoroallyloxy)-N-tert-butylbenzamide hydrochloride as defined hereinafter is used. An "active ingredient" is also sometimes referred to herein as an "active substance" or as "active pharmaceutical ingredient" or "API".

(E)-4-(2-(aminomethyl)-3-fluoroallyloxy)-N-tert-butylbenzamide and its salts as well as methods of their synthesis are described for example in the following patent application: WO 2013/163675 (compound 23).

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventivally treating" and "preventing" are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the before-mentioned types of tablets may be without or with one or more coatings. The term "tablet" also comprises mini, melt, chewable and orally disintegrating tablets.

The terms "pharmacopoe" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

DETAILED DESCRIPTION

The aspects according to the present invention, in particular the pharmaceutical compositions, methods and uses, refer to (E)-4-(2-(aminomethyl)-3-fluoroallyloxy)-N-tert-butylbenzamide having the following chemical structure

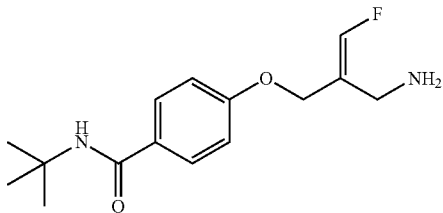 [SMILES: CC(C)(C)NC(=O)c1ccc(OC/C(=C/F)CN)cc1]

or a pharmaceutically acceptable salt thereof as active pharmaceutical ingredient, particularly to (E)-4-(2-(aminomethyl)-3-fluoroallyloxy)-N-tert-butylbenzamide hydrochloride.

According to an embodiment of the invention the pharmaceutical composition or the pharmaceutical dosage form comprises only one active pharmaceutical ingredient being the compound (E)-4-(2-(aminomethyl)-3-fluoroallyloxy)-N-tert-butylbenzamide or a pharmaceutically acceptable salt thereof.

According to this invention, it is to be understood that the definitions of the compound also comprise its hydrates, solvates and polymorphic forms thereof, and prodrugs thereof.

Figure 2:
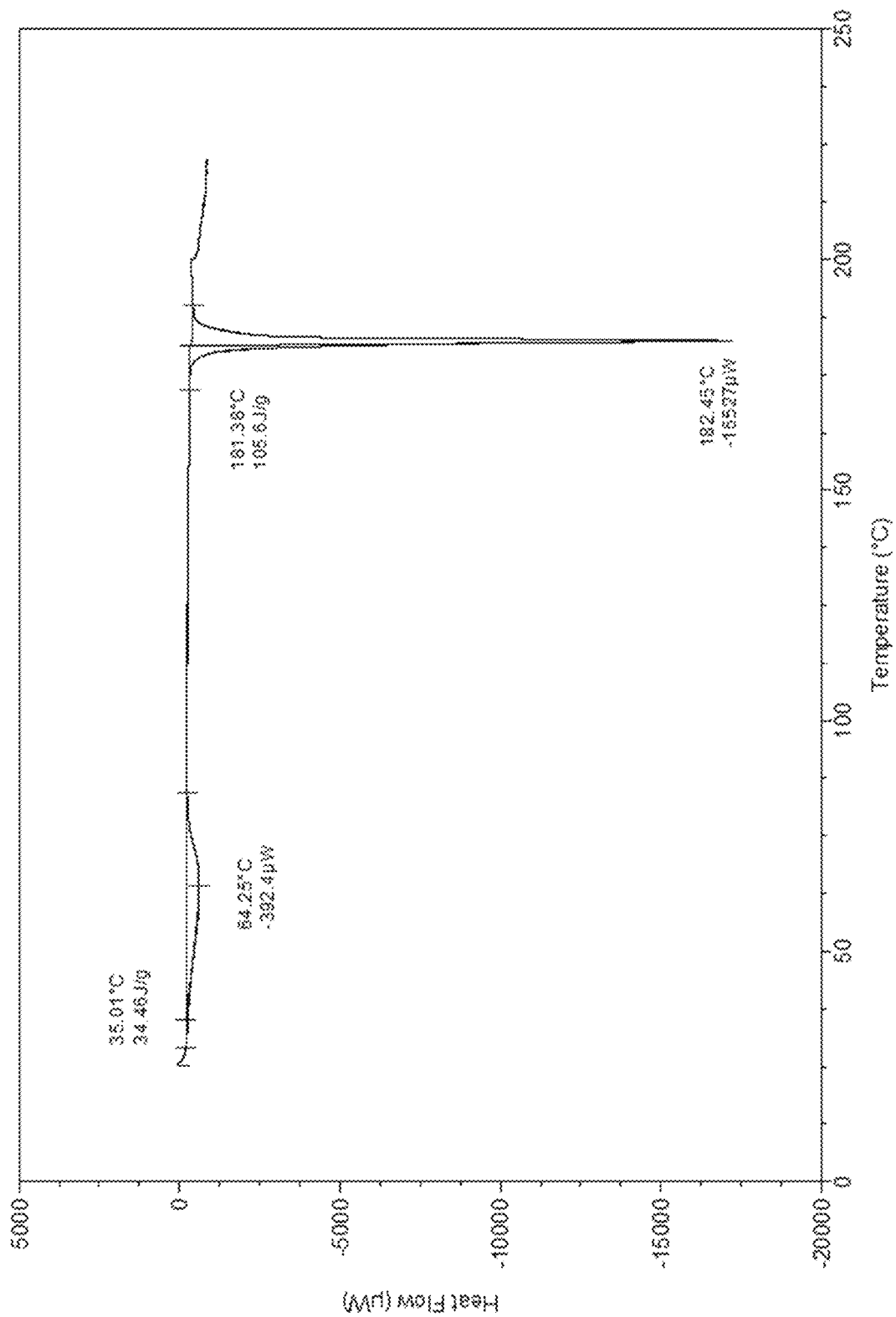
FIG. 2: DSC curve of Form I of (E)-4-(2-(aminomethyl)-3-fluoroallyloxy)-N-tert-butylbenzamide hydrochloride.

A preferred solid form of compound (E)-4-(2-(aminomethyl)-3-fluoroallyloxy)-N-tert-butylbenzamide hydrochloride is "Form I", a crystalline, high-melting, stable form of (E)-4-(2-(aminomethyl)-3-fluoroallyloxy)-N-tert-butylbenzamide hydrochloride that is not prone to polymorphic conversions. Form I is found to contain water: The molar ratio of (E)-4-(2-(aminomethyl)-3-fluoroallyloxy)-N-tert-butylbenzamide hydrochloride relative to $H_2O$ is in the range from 3:1 to 5:1, more specifically it is 4:1; Form I could therefore be considered to be a tetartohydrate. The X-ray powder diffraction (XRPD) peaks of Form I are given in section Examples and Experimental Data. Hence, in particular, Form I is characterized by an XRPD pattern comprising peaks at 3.82, 7.63, 13.55 and 15.29 degrees 2θ, specifically comprising peaks at 3.82, 7.63, 13.55, 15.29, 16.03 and 17.80 degrees 2θ, more specifically comprising peaks at 3.82, 7.63, 11.46, 13.55, 15.29, 16.03, 17.80 and 19.02 degrees 2θ, (for all peaks mentioned above: ±0.2 degrees 2θ, using CuKα radiation). Form I is furthermore characterized by a melting point of about 181° C.±5° C. (determined via differential scanning calorimetry (DSC); evaluated as onset-temperature; heating rate 10° C./min). The DSC curve of Form I is depicted in FIG. 2. Form I of (E)-4-(2-(aminomethyl)-3-fluoroallyloxy)-N-tert-butylbenzamide hydrochloride may be obtained by recrystallization of (E)-4-(2-(aminomethyl)-3-fluoroallyloxy)-N-tert-butylbenzamide hydrochloride as synthesized according to methods known in the art.

Recrystallization of (E)-4-(2-(aminomethyl)-3-fluoroallyloxy)-N-tert-butylbenzamide hydrochloride may advantageously be performed from solvent systems selected from the group consisting of water/ethanol/ethyl acetate, water/isopropyl alcohol/ethyl acetate, isopropyl alcohol/ethyl acetate/MTBE, methanol/ethyl acetate, water/isopropyl acetate/acetone and water/isopropyl alcohol/heptane, preferably selected from water/ethanol/ethyl acetate, water/isopropyl alcohol/ethyl acetate and isopropyl alcohol/ethyl acetate/MTBE; more preferably the solvent system is isopropyl alcohol/ethyl acetate/MTBE wherein the volume ratio of isopropyl alcohol and ethyl acetate is in the range from about 1:1 to about 1:0.75 and wherein the volume ratio of isopropyl alcohol and MTBE is in the range from about 1:0.9 to about 1:0.65, e.g. the volume ratio of the three components is 9:8:7.

Form I of (E)-4-(2-(aminomethyl)-3-fluoroallyloxy)-N-tert-butylbenzamide hydrochloride is isolated from solution by means known to the one skilled in the art which comprise, but are not limited to centrifugation and filtration. In particular, (E)-4-(2-(aminomethyl)-3-fluoroallyloxy)-N-tert-butylbenzamide hydrochloride is isolated by a method comprising filtration, washing of the filter cake and drying under vacuum. The obtained crystals are preferably washed with a solvent or a mixture of solvents, wherein the solvent is preferably selected from MTBE and a 3:1 (v/v) mixture of heptane/isopropyl alcohol followed by heptane. The most preferred solvent is MTBE. Preferably, remaining solvent(s) are advantageously removed from the crystals in a drying step under vacuum, for example at about 60° C. for about 5 to 12 hours. The temperature, the pressure and the duration of this drying step may be chosen in order to lower the content of one or more residual solvents below a given value.

The pharmaceutical composition or pharmaceutical dosage form according to the invention preferably comprises (E)-4-(2-(aminomethyl)-3-fluoroallyloxy)-N-tert-butylbenzamide hydrochloride present in its Form I as defined hereinbefore and hereinafter.

In one embodiment, the active ingredient represents 25% or less of the weight of the pharmaceutical composition. Preferably, the active ingredient represents 0.5% to 25% of the weight of the pharmaceutical composition. More preferably, the active ingredient represents 1.0% to 15% of the weight of the pharmaceutical composition. Even more preferably, the active ingredient represents 3.5% to 10% of the weight of the pharmaceutical composition. According to another embodiment the active ingredient represents 1.5% to 10% of the weight of the pharmaceutical composition.

A pharmaceutical composition according to the invention comprises one or more stabilizers.

The stabilizer is preferably an acidic stabilizer, in particular an acid. Preferably the stabilizer is an organic acid, more preferably a diprotic, in particular a dicarboxylic organic acid, for example comprising 3-10, in particular 4-8 or 4-6 C-atoms which may comprise one or more hydroxy groups, for example alpha-hydroxy groups. The organic acid may be an amino acid, in particular an amino acid hydrochloride. More preferably the stabilizer is selected from the group consisting of L-glutamic acid hydrochloride, fumaric acid and tartaric acid. Preferred examples of the stabilizer are L-glutamic acid hydrochloride and tartaric acid. In one embodiment, L-glutamic acid hydrochloride is used as stabilizer. In another embodiment, tartaric acid is used as stabilizer. In still another embodiment, fumaric acid is used as stabilizer.

In one embodiment, the stabilizer represents 20% or less of the weight of the pharmaceutical composition. In one embodiment, the stabilizer represents 0.5% or more of the weight of the pharmaceutical composition. Preferably, the stabilizer represents 1% to 15% of the weight of the pharmaceutical composition. More preferably, the stabilizer represents 1% to 10% of the weight of the pharmaceutical composition. According to an embodiment of this invention the stabilizer represents 1% to 5% of the weight of the pharmaceutical composition. According to another embodiment of this invention the stabilizer represents 2% to 5% of the weight of the pharmaceutical composition.

In one embodiment, the molar ratio of the stabilizer to the active ingredient is about 30:1 or less, in particular about 10:1 or less, for example about 5:1 or less. In one embodiment, the molar ratio of the stabilizer to the active ingredient is about 1:5 or more, in particular about 1:4 or more, for example about 1:3 or more, or for example about 1:2 or more. According to an aspect of this embodiment, the molar ratio of the stabilizer to the active ingredient is in the range of about 1:3 to about 20:1. According to another aspect of this embodiment, the molar ratio of the stabilizer to the active ingredient is in the range of about 1:3 to about 10:1 or about 1:2 to about 5:1.

In one aspect the present invention provides a pharmaceutical composition comprising (E)-4-(2-(aminomethyl)-3-fluoroallyloxy)-N-tert-butylbenzamide or a pharmaceutically acceptable salt thereof, particularly a pharmaceutical composition comprising (E)-4-(2-(aminomethyl)-3-fluoroallyloxy)-N-tert-butylbenzamide hydrochloride as active pharmaceutical ingredient, and one or more, preferably one stabilizer as defined hereinbefore and one or more excipients.

In the following the suitable excipients in the pharmaceutical composition according to the invention are described in further detail.

Preferably, the pharmaceutical composition according to the invention additionally comprises one or more diluents. Suitable diluents (also referred to as fillers) according to the invention are for example, lactose, in particular lactose monohydrate, cellulose and derivatives, such as powdered cellulose, microcrystalline or silicified microcrystalline cellulose, cellulose acetate, starches and derivatives such as pregelatinized starch, corn starch, wheat starch, rice starch, potato starch, sterilizable maize, sodium chloride, calcium carbonate, calcium phosphate, particularly dibasic calcium phosphate, calcium sulphate, dicalcium or tricalcium phosphate, magnesium carbonate, magnesium oxide, sugars and derivatives such as confectioner's sugar, fructose, sucrose, dextrates, dextrin, D-sorbitol sulfobutylether β-cyclodextrin, dextrose, polydextrose, trehalose, maltose, maltitol, mannitol, maltodextrin, sorbitol, inulin, xylitol, erythritol, isomalt, kaolin and lactitol. According to an embodiment of the present invention the diluent is mannitol.

The pharmaceutical composition according to the present invention may also comprise one or more lubricants. Suitable lubricants according to the invention are stearic acid as well as salts thereof, particularly alkali and earth alkali salts thereof, including sodium stearate, calcium stearate, zinc stearate, magnesium stearate, sodium stearyl fumarate and glyceryl monostearate. A preferred lubricant is magnesium stearate. Such lubricant may be present in a concentration of 0.25-5%, preferably 0.5-2% in said pharmaceutical composition or pharmaceutical dosage form.

Optionally, the pharmaceutical composition according to the invention further comprises one or more binders. Any binder usually employed in pharmaceutical compositions may be used in the context of the instant invention. Binders are for example naturally occurring or partially or totally synthetic polymers selected from acacia, agar, alginic acid, carbomers, carmellose sodium, carrageenan, cellulose acetate phthalate, *ceratonia*, chitosan, confectionar's sugar, copovidone, povidone, cottonseed oil, dextrate, dextrin, dextrose, polydextrose, maltodextrin, maltose, cellulose and derivatives thereof such as microcrystalline cellulose, methylcellulose, ethylcellulose, hydroxyethyl cellulose, hydroxyethyl methylcellulose, hydroxypropyl celluloses, carboxymethylcelluloses, hypromelloses (cellulose hydroxypropyl methyl ether), starch and derivatives thereof, such as pregelatinized starch, hydroxypropylstarch, corn starch, gelatin, glyceryl behenate, tragacanth, guar gum, hydrogenated vegetable oils, inulin, poloxamer, polycarbophils, polyethylene oxide, polyvinylpyrrolidone, copolymers of N-vinylpyrrolidone and vinyl acetate, polymethacrylates, polyethylene glycols, alginates such as sodium alginate, gelatin, sucrose, sunflower oil, zein as well as derivatives and mixtures thereof.

Optionally, the pharmaceutical composition according to the invention further comprises one or more disintegrants. Suitable disintegrants according to the invention are for example powdered cellulose, crospovidone, croscarmellose sodium, docusate sodium, low-substituted hydroxypropyl cellulose, magnesium aluminum silicate, microcrystalline cellulose, polacrilin potassium, sodium starch glycolate, starch, particularly pregelatinized starch and corn starch.

Finally, optional additional additives such as colorants or flavouring agents can be used.

In one embodiment, the pharmaceutical composition or pharmaceutical dosage form, for example tablet, comprises:

| | Amount (% by weight) |
|---|---|
| Active ingredient | 0.5-25 |
| One or more Stabilizers | 0.5-15 |
| One or more Diluents | 60-98.5 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 1.0-15 |
| One or more Stabilizers | 1.0-10 |
| One or more Diluents | 70-98 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 1.5-10 |
| One or more Stabilizers | 1-5 |
| One or more Diluents | 85-95 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 3.5-10 |
| One or more Stabilizers | 1-5 |
| One or more Diluents | 85-95 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 0.5-25 |
| One or more Stabilizers | 0.5-10 |
| One or more Diluents | 60-99 |
| Lubricant | 0.25-5.0 |
| Optionally Additional additives | ad 100% |

In one aspect, the active ingredient is (E)-4-(2-(aminomethyl)-3-fluoroallyloxy)-N-tert-butylbenzamide hydrochloride.

In one embodiment, the pharmaceutical composition or pharmaceutical dosage form, for example tablet, comprises:

| | Amount (% by weight) |
|---|---|
| Active ingredient | 0.5-25 |
| L-Glutamic acid hydrochloride | 1.0-10 |
| Mannitol | 63-98 |
| Magnesium stearate | 0.5-2.0 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 3.5-10 |
| L-Glutamic acid hydrochloride | 1.0-5.0 |
| Mannitol | 83-94 |
| Magnesium stearate | 0.5-2.0 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 0.5-25 |
| Tartaric acid | 1.0-10 |
| Mannitol | 63-98 |
| Magnesium stearate | 0.5-2.0 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 3.5-10 |
| Tartaric acid | 1.0-5.0 |
| Mannitol | 83-94 |
| Magnesium stearate | 0.5-2.0 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 1.5-10 |
| Tartaric acid | 1.0-5.0 |
| Mannitol | 83-94 |
| Magnesium stearate | 0.5-2.0 |
| Optionally Additional additives | ad 100% |

In one aspect, the active ingredient is (E)-4-(2-(aminomethyl)-3-fluoroallyloxy)-N-tert-butylbenzamide hydrochloride.

In another embodiment, the pharmaceutical composition or pharmaceutical dosage form, for example tablet, comprises:

| | Amount (% by weight) |
|---|---|
| Active ingredient | 0.5-25 |
| Fumaric acid | 1.0-10 |
| Mannitol | 63-98 |
| Magnesium stearate | 0.5-2.0 |
| Optionally Additional additives | ad 100% |

In one aspect, the active ingredient is (E)-4-(2-(aminomethyl)-3-fluoroallyloxy)-N-tert-butylbenzamide hydrochloride.

In one embodiment, the pharmaceutical composition or pharmaceutical dosage form, for example tablet, comprises:

| | Amount (% by weight) |
|---|---|
| Active ingredient | 3.5-10 |
| Fumaric acid | 1.0-5.0 |
| Mannitol | 78-91 |
| Magnesium stearate | 0.5-2.0 |
| Optionally Additional additives | ad 100% |

In one aspect, the active ingredient is (E)-4-(2-(aminomethyl)-3-fluoroallyloxy)-N-tert-butylbenzamide hydrochloride.

The pharmaceutical composition may be formulated in the form of tablets, granules, fine granules, powders, capsules, caplets, soft capsules, pills, chewable tablets, troches, fast dissolving tablets, oral fast-dispersing tablets, etc.

Preferably, the pharmaceutical composition according to the invention is a immediate release formulation.

In one aspect, the pharmaceutical composition according to the invention is a solid pharmaceutical composition, for example a solid pharmaceutical composition for oral administration.

A dosage form according to the invention may be a tablet. Said tablet may optionally be film-coated. Typically a film coat represents 2-5% by weight of the total composition and comprises preferably a film-forming agent, a plasticizer, an anti-tacking agent and optionally one or more pigments. An exemplary coat composition may comprise hydroxypropyl methylcellulose (HPMC), polyethylene glycol (PEG), talc, titanium dioxide and optionally iron oxide, including iron oxide red and/or yellow.

For example, a film coat according of the present invention comprises 48% hypromellose, 14% macrogol, 18% titanium oxide, 18% talc and 2% iron oxide red (Opadry® red 02F250006 INT).

In one aspect, a film coat according to the present invention comprises

| | Amount (% by weight) |
|---|---|
| Film-forming agent | 30-70 |
| One or more plasticizers | 1-20 |
| One or more anti-tacking agents | 5-30 |
| One or more colorants | 0-30 |
| Optionally additional additives | ad 100% |

In order to balance both stability and manufacturability of the pharmaceutical compositions and pharmaceutical dosage forms according to the invention, the exact ranges of the ingredients, particularly of the stabilizer and the lubricant, may be optimized by methods well known to one skilled in the art.

In another aspect, the present invention provides a direct compression process for making a pharmaceutical composition, wherein said process comprises the steps of:
(1) Premixing the active ingredient and the main portion of the excipients and stabilizer(s) in a mixer to obtain a pre-mixture;
(2) optionally dry screening the pre-mixture through a screen in order to segregate cohesive particles and to improve content uniformity;
(3) mixing the pre-mixture of step (1) or (2) in a mixer, optionally by adding remaining excipients to the mixture and continuing mixing;
(4) tableting the final mixture of step (3) by compressing it on a suitable tablet press to produce the tablet cores;
(5) optionally film-coating of the tablet cores of step (4) with a film coat.

In another aspect, the present invention provides a pharmaceutical composition obtainable by the above process.

In another aspect, the present invention provides a dry granulation process for making a pharmaceutical composition, wherein said process comprises the steps of:
(1) mixing the active ingredient with either all or a portion of the excipients and stabilizer(s) in a mixer;
(2) compaction of the mixture of step (1) on a suitable roller compactor;
(3) reducing the ribbons obtained during step (2) to granules, preferably small granules, by suitable milling or sieving steps;
(4) optionally mixing the granules of step (3) with the remaining excipients in a mixer to obtain the final mixture;
(5) tabletting the granules of step (3) or the final mixture of step (4) by compressing it on a suitable tablet press to produce the tablet cores;
(6) optionally film-coating of the tablet cores of step (5) with a film coat.

In another aspect, the present invention provides a pharmaceutical composition obtainable by the above process.

In addition to the above-mentioned processes, the pharmaceutical compositions and pharmaceutical dosage forms according to the invention can also be prepared by other methods known to one skilled in the art, such as by wet granuation processes. The pharmaceutical compositions according to the invention allow a storage of more than 12 months, preferably of up to 36 months at room temperature, for example at 20° C. No detrimental degradation of the active ingredient is observed under these storage conditions. Therefore, there is no need for storing the pharmaceutical compositions according to the invention at temperatures below 8° C.

The pharmaceutical compositions according to the invention allow a high content uniformity and an effective production with regard to time and costs of pharmaceutical dosage forms, such as tablets and capsules. Furthermore, in one embodiment, these pharmaceutical dosage forms are in particular tablets.

Therefore, in another aspect the present invention provides a pharmaceutical dosage form comprising a pharmaceutical composition according to the invention. In one aspect, the pharmaceutical dosage form according to the invention is a solid pharmaceutical dosage form, for example a solid pharmaceutical dosage form for oral administration.

In another aspect, the present invention provides a process for the preparation of a pharmaceutical dosage form according to the invention comprising one or more granulation processes, wherein the active pharmaceutical ingredient together with one or more excipients is granulated.

In another aspect, the present invention provides a process for the preparation of a pharmaceutical dosage form according to the invention comprising one or more direct compression processes.

It can be found that a pharmaceutical composition or a pharmaceutical dosage form comprising (E)-4-(2-(aminomethyl)-3-fluoroallyloxy)-N-tert-butylbenzamide or a pharmaceutically acceptable salt thereof, particularly a pharmaceutical composition or a pharmaceutical dosage form comprising (E)-4-(2-(aminomethyl)-3-fluoroallyloxy)-N-tert-butylbenzamide hydrochloride, can advantageously be used for preventing, slowing progression of, delaying or treating one or more diseases as described hereinbefore and hereinafter in patients.

According to an aspect the invention relates to a method for preventing, slowing the progression of, delaying or treating of one or more fibrotic diseases, metabolic diseases, inflammatory diseases, ocular diseases, neuroinflammatory diseases or cancers in a patient in need thereof characterized in that a pharmaceutical composition or pharmaceutical dosage form as defined hereinbefore and hereinafter is administered to the patient.

According to an embodiment of this aspect the invention relates to a method for preventing, slowing the progression of, delaying or treating of a fibrotic disease selected from the group consisting of cystic fibrosis, interstitial lung disease, including idiopathic pulmonary fibrosis, liver fibrosis including non-alcoholic steatohepatitis (NASH), alcohol induced fatty liver, alcohol induced liver fibrosis, toxic fatty liver and cirrhosis of the liver, kidney fibrosis, scleroderma, radiation-induced fibrosis and other diseases where excessive fibrosis contributes to disease pathology in a patient in need thereof characterized in that a pharmaceutical composition or pharmaceutical dosage form as defined hereinbefore and hereinafter is administered to the patient.

According to an embodiment of this aspect the invention relates to a method for preventing, slowing the progression of, delaying or treating of a metabolic disease selected from the group consisting of pre-diabetes mellitus, type 1 diabetes mellitus, type 2 diabetes mellitus, complications associated with diabetes mellitus, overweight, obesity, impaired glucose tolerance (IGT), impaired fasting blood glucose (IFG), hyperglycemia, postprandial hyperglycemia, insulin resistance, fatty liver, including non-alcoholic fatty liver disease (NAFLD), overweight, obesity, metabolic syndrome in a patient in need thereof characterized in that a pharmaceutical composition or pharmaceutical dosage form as defined hereinbefore and hereinafter is administered to the patient.

Complications associated with diabetes mellitus include cataracts and micro- and macrovascular diseases, such as diabetic nephropathy, glomerulosclerosis, diabetic retinopathy, choroidal neovascularisation, non-alcoholic fatty liver (NAFL) disease, non-alcoholic steatohepatitis (NASH), diabetic neuropathy, diabetic pain, tissue ischaemia, diabetic foot, diabetic ulcer, arteriosclerosis, myocardial infarction, accute coronary syndrome, unstable angina pectoris, stable angina pectoris, stroke, peripheral arterial occlusive disease, cardiomyopathy, heart failure, cardiovascular death, heart rhythm disorders and vascular restenosis.

According to another embodiment of this aspect the invention relates to a method for preventing, slowing the progression of, delaying or treating a treating of an inflammation disease selected from the group consisting of arthritis (including juvenile rheumatoid arthritis), Crohn's disease, ulcerative colitis, inflammatory bowel diseases (e.g. irritable bowel disease), psoriasis, asthma (e.g. eosinophilic asthma, severe asthma, virally exacerbated asthma), pulmonary inflammation, chronic pulmonary obstructive disease (COPD), bronchiectasis, skin inflammation, ocular disease, contact dermatitis, liver inflammation, liver autoimmune diseases, autoimmune hepatitis, primary biliary cirrhosis, sclerosing cholangitis, autoimmune cholangitis, alcoholic liver disease, artherosclerosis, chronic heart failure, congestive heart failure, ischemic diseases, stroke and complications thereof, myocardial infarction and complications thereof, inflammatory cell destruction following stroke, synovitis, systemic inflammatory sepsis, inflammation due to diabetes, lung inflammation associated with cystic fibrosis, other bacteria-induced lung diseases such as sepsis, acute respiratory distress syndrome (ARDS), acute lung injury (ALI), transfusion induced lung injury (TRALI) in a patient in need thereof characterized in that a pharmaceutical composition or pharmaceutical dosage form as defined hereinbefore and hereinafter is administered to the patient.

According to another embodiment of this aspect the invention relates to a method for preventing, slowing the progression of, delaying or treating an ocular disease, including macular degeneration, including diabetic macular edema, uveitis and retinopathy, including diabetic retinopathy, in a patient in need thereof characterized in that a pharmaceutical composition or pharmaceutical dosage form as defined hereinbefore and hereinafter is administered to the patient.

According to another embodiment of this aspect the invention relates to a method for preventing, slowing the progression of, delaying or treating of a neuroinflammatory disorder selected from the group consisting of stroke, Parkinson's disease, Alzheimer's disease, vascular dementia, multiple sclerosis, chronic multiple sclerosis in a patient in need thereof characterized in that a pharmaceutical composition or pharmaceutical dosage form as defined hereinbefore and hereinafter is administered to the patient.

According to another embodiment of this aspect the invention relates to a method for preventing, slowing the progression of, delaying or treating a cancer selected from the group consisting of lung cancer, breast cancer, colorectal cancer, anal cancer, pancreatic cancer, prostate cancer, ovarian carcinoma, liver and bile duct carcinoma, esophageal carcinoma, non-Hodgkin's lymphoma, bladder carcinoma, carcinoma of the uterus, glioma, glioblastoma, medullablastoma, and other tumors of the brain kidney cancer, cancer of the head and neck, cancer of the stomach, multiple myeloma, testicular cancer, germ cell tumor, neuroendocrine tumor, cervical cancer, carcinoids of the gastrointestinal tract, breast, and other organs; signet ring cell carcinoma, mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma in a patient in need thereof characterized in that a pharmaceutical composition or pharmaceutical dosage form as defined hereinbefore and hereinafter is administered to the patient.

According to another aspect the present invention relates to a method for treating of non-alcoholic fatty liver disease (NAFLD) or non-alcoholic steatohepatitis (NASH), in particular of NASH with liver fibrosis, for example of NASH with liver fibrosis stages 2 and 3, in a patient in need thereof characterized in that a pharmaceutical composition comprising (E)-4-(2-(aminomethyl)-3-fluoroallyloxy)-N-tert-butylbenzamide or a pharmaceutically acceptable salt thereof as an active pharmaceutical ingredient (API), preferably a pharmaceutical composition according to this invention, is administered to the patient. For example the patient is a patient with NAS (NAFLD activity score) greater or equal than 4. Preferred doses of the API for once daily oral administration are 1 mg, 2 mg, 2.5 mg, 3 mg, 4 mg, 5 mg, 6 mg, 7 mg, 7.5 mg, 8 mg, 9 mg, 10 mg, 12.5 mg, 15 mg, 20 mg or 25 mg, in particular 3 mg, 5 mg, 6 mg or 10 mg related to (E)-4-(2-(aminomethyl)-3-fluoroallyloxy)-N-tert-butylbenzamide. According to an embodiment of this aspect of the invention the pharmaceutical composition comprises (E)-4-(2-(aminomethyl)-3-fluoroallyloxy)-N-tert-butylbenzamide or a pharmaceutically acceptable salt thereof as the only one active pharmaceutical ingredient.

The effect of an administration of said pharmaceutical composition to a patient with NAFLD, NASH and/or liver fibrosis may be observed by a change, in particular reduction of relevant biomarkers of liver inflammation and/or liver function, such as for example ALT (alanine aminotransferase), AST (aspartate aminotransferase), AP (alkaline phosphatase), gamma-GT (gamma-glutamil transferase), CK-18 (cytokeratin 18) fragments or HVPG (hepatic vein pressure gradient).

Furthermore the effect of an administration of said pharmaceutical composition to a patient with NAFLD, NASH and/or liver fibrosis may be observed by an improvement of for example the degree or stage of steatosis, fibrosis, liver stiffness or health-related quality of life.

The effects of (E)-4-(2-(aminomethyl)-3-fluoroallyloxy)-N-tert-butylbenzamide observed on in vivo models of ocular diseases indicate an improvement of neuronal function and prevention of pathologic neoangiogenesis and thus argue for a prevention of loss of visual acuity and neovascularization. The data which are described in the experimental section support a use of the active ingredient in methods for treating of patients with diabetic retinopathy, including non-proliferative and proliferative diabetic retinopathy, and preventing a progression to proliferative diabetic retinopathy.

According to a further aspect the present invention relates to a method for treating of diabetic retinopathy in a patient in need thereof characterized in that a pharmaceutical composition comprising (E)-4-(2-(aminomethyl)-3-fluoroallyloxy)-N-tert-butylbenzamide or a pharmaceutically acceptable salt thereof as an active pharmaceutical ingredient (API), preferably a pharmaceutical composition according to this invention, is administered to the patient, in particular to the patient without diabetic macular edema. Preferred doses of the API for oral administration once daily or per day are from 1 to 25 mg, more preferably from 2.5 to 15 mg or 5 to 12.5 mg, most preferably from 2.5 to 10 mg or 5 to 10 mg, in particular 2.5 mg, 3 mg, 5 mg, 6 mg, 7.5 mg, 10 mg or 12.5 mg, for example 5 mg, 7.5 mg or 10 mg, all amounts related to (E)-4-(2-(aminomethyl)-3-fluoroallyloxy)-N-tert-butylbenzamide as free base. Preferred doses of the API for once daily oral administration are 1 mg, 2 mg, 2.5 mg, 3 mg, 4 mg, 5 mg, 6 mg, 7 mg, 7.5 mg, 8 mg, 9 mg, 10 mg, 12.5 mg, 15 mg, 20 mg or 25 mg, in particular 3 mg, 5 mg, 6 mg or 10 mg, for example 10 mg related to (E)-4-(2-(aminomethyl)-3-fluoroallyloxy)-N-tert-butylbenzamide. According to an embodiment of this aspect of the invention the pharmaceutical composition comprises (E)-4-(2-(aminomethyl)-3-fluoroallyloxy)-N-tert-butylbenzamide or a pharmaceutically acceptable salt thereof as the only one active pharmaceutical ingredient.

According to an embodiment of this aspect the patient has diabetes mellitus, for example diabetes mellitus type 1 or type 2.

According to an embodiment of this aspect the diabetic retinopathy is a non-proliferative diabetic retinopathy (NPDR) wherein the patient does not have diabetic macular edema (DME), in particular the patient does not have center-involved diabetic macular edema (CI-DME). For example the patient has moderately or severe NPRD without CI-DME or the patient has NPDR without CI-DME and an NPRD level 47 or 53 as determined by using the diabetic retinopathy severity scale (DRSS). Preferred and exemplified doses are described hereinbefore with regard to the method for treating of diabetic retinopathy.

According to another embodiment of this aspect the present invention relates to a method for improving retinal lesions in a patient with diabetic retinopathy, in particular in a patient with non-proliferative diabetic retinopathy (NPDR) wherein the patient does not have diabetic macular edema (DME), in particular wherein the patient does not have center-involved diabetic macular edema (CI-DME), characterized in that a pharmaceutical composition comprising (E)-4-(2-(aminomethyl)-3-fluoroallyloxy)-N-tert-butylbenzamide or a pharmaceutically acceptable salt thereof as an active pharmaceutical ingredient (API), preferably a pharmaceutical composition according to this invention, is administered to the patient. For example the patient has moderately or severe NPRD without CI-DME or the patient has NPDR without CI-DME and an NPRD level 47 or 53 as determined by using the diabetic retinopathy severity scale (DRSS). The improvement of the diabetic retinopathy, in particular of retinal lesions, may be determined for example by using the diabetic retinopathy severity scale (DRSS). Alternatively an improvement of the eye may be determined according to best corrected visual acuity (BCVA). Preferred and exemplified doses are described hereinbefore with regard to the method for treating of diabetic retinopathy. According to this embodiment the pharmaceutical composition may comprise (E)-4-(2-(aminomethyl)-3-fluoroallyloxy)-N-tert-butylbenzamide or a pharmaceutically acceptable salt thereof as the only one active pharmaceutical ingredient.

According to another embodiment of this aspect the diabetic retinopathy is a non-proliferative diabetic retinopathy wherein the patient has diabetic macular edema (DME).

According to an embodiment of this aspect the diabetic retinopathy is a proliferative diabetic retinopathy wherein the patient does not have diabetic macular edema (DME). According to another embodiment of this aspect the diabetic retinopathy is a proliferative diabetic retinopathy wherein the patient has diabetic macular edema (DME).

According to an embodiment of this aspect of the invention the method comprises preventing, reversing, delaying, reducing or stopping a progression from non-proliferative diabetic retinopathy (NPDR) to proliferative diabetic retinopathy in the patient, in particular in a patient without diabetic macular edema (DME), in particular wherein the patient does not have center-involved diabetic macular edema (CI-DME). For example the patient has moderately or severe NPRD without CI-DME or the patient has NPDR without CI-DME and an NPRD level 47 or 53 as determined by using the diabetic retinopathy severity scale (DRSS). Preferred and exemplified doses are described hereinbefore with regard to the method for treating of diabetic retinopathy.

According to an embodiment of this aspect of the invention the method comprises preventing, reversing, delaying, reducing or stopping a progression from non-proliferative diabetic retinopathy (NPDR) or proliferative diabetic retinopathy (PDR) to diabetic macular edema (DME), in particular central-involved diabetic macular edema in the patient, in particular in a patient without diabetic macular edema. Preferred and exemplified doses are described hereinbefore with regard to the method for treating of diabetic retinopathy.

According to an embodiment of this aspect of the invention the method comprises preventing, reversing, delaying, reducing or stopping a neovascularization in a patient, in particular in a patient without diabetic macular edema. According to an example of this embodiment the patient has diabetic retinopathy, in particular non-proliferative diabetic retinopathy. Preferred and exemplified doses are described hereinbefore with regard to the method for treating of diabetic retinopathy.

Via an administration of the API to the patient a reduction of retinal oxidative stress, hypoxia, inflammation, angiogenesis, advanced glycation endproducts may be observed leading to a stabilization and/or healing of diabetic retinopathy.

The effect of an administration of said pharmaceutical composition to a patient with diabetic retinopathy, e.g. non-proliferative or proliferative diabetic retinopathy, may be observed by an improvement of BCVA (best corrected visual acuity), in the diabetic retinopathy severity scale (DRSS), health-related quality of life or an improvement in the need for rescue treatment, like PRP (panretinal photocoagulation), anti-VEGF and/or treatment for complications of diabetic retinopathy, like glaucoma, vitreous bleeding and retinal detachment.

The pharmaceutical compositions and methods according to this invention show advantageous effects in the treatment and prevention of those diseases and conditions as described hereinbefore. Advantageous effects may be seen for example with respect to efficacy, dosage strength, dosage frequency, pharmacodynamic properties, pharmacokinetic properties, fewer adverse effects, convenience, compliance, etc.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older.

In the following, preferred ranges of the amount of (E)-4-(2-(aminomethyl)-3-fluoroallyloxy)-N-tert-butylbenzamide or a pharmaceutically acceptable salt thereof to be employed in the pharmaceutical compositions, pharmaceutical dosage forms or methods according to this invention are described. These ranges refer to the amounts to be administered per day with respect to an adult patient, in particular to a human being, for example of approximately 70 kg body weight, and can be adapted accordingly with regard to an administration 2, 3, 4 or more times daily and with regard to other routes of administration and with regard to the age of the patient. The ranges of the dosage and amounts are calculated for the active ingredient (E)-4-(2-(aminomethyl)-3-fluoroallyloxy)-N-tert-butylbenzamide.

A preferred amount of (E)-4-(2-(aminomethyl)-3-fluoroallyloxy)-N-tert-butylbenzamide, which may be employed as a pharmaceutically acceptable salt thereof, in particular as (E)-4-(2-(aminomethyl)-3-fluoroallyloxy)-N-tert-butylbenzamide hydrochloride, is in a range from 0.5 to 25 mg (related to the basic compound, i.e. to (E)-4-(2-(aminomethyl)-3-fluoroallyloxy)-N-tert-butylbenzamide), preferably from 1 to 20 mg, even more preferably from 1 to 10 mg, for example 3 to 10 mg. A preferred doses of (E)-4-(2-(aminomethyl)-3-fluoroallyloxy)-N-tert-butylbenzamide is for example 1 mg, 2 mg, 2.5 mg, 3 mg, 4 mg, 5 mg, 6 mg, 7 mg, 7.5 mg, 8 mg, 9 mg, 10 mg, 12.5 mg, 15 mg, 20 mg or 25 mg, in particular 2.5 mg, 3 mg, 5 mg, 6 mg or 10 mg. All amounts in mg are preferably related to the basic compound, (E)-4-(2-(aminomethyl)-3-fluoroallyloxy)-N-tert-butylbenzamide, i.e. to the API as free base.

According to an embodiment a pharmaceutical composition according to the invention comprises (E)-4-(2-(aminomethyl)-3-fluoroallyloxy)-N-tert-butylbenzamide or a pharmaceutically acceptable salt thereof, in particular (E)-4-(2-(aminomethyl)-3-fluoroallyloxy)-N-tert-butylbenzamide hydrochloride, as active pharmaceutical ingredient and one or more stabilizers, in particular one stabilizer, selected from L-glutamic acid hydrochloride and tartaric acid, in particular tartaric acid, wherein the amount of the active ingredient is in the range from 0.5 to 25% by weight of the pharmaceutical composition, and wherein the molar ratio of the stabilizer to the active ingredient is in the range from about 1:3 to about 20:1, in particular about 1:2 to about 10:1, and one or more excipients, for example one or more diluents. A preferred amount of the one or more diluents is from 70 to 98% by weight of the pharmaceutical composition. In addition the pharmaceutical composition may comprise additional additives, for example one or more lubricants.

According to an embodiment a pharmaceutical dosage form according to the present invention is a solid pharmaceutical dosage form comprising the pharmaceutical composition according to the embodiment described hereinbefore wherein the amount of the active pharmaceutical ingredient is in the range from 1 to 10 mg, for example 1, 2.5, 3, 5, 6 or 10 mg, related to the basic compound, (E)-4-(2-(aminomethyl)-3-fluoroallyloxy)-N-tert-butylbenzamide, i.e. to the active ingredient as free base. According to an aspect of this embodiment the solid pharmaceutical dosage form is a tablet, for example a film-coated tablet.

The application of the pharmaceutical composition or dosage form may occur up to three times a day, preferably one or two times a day, most preferably once a day.

Within the scope of the present invention, the pharmaceutical composition is preferably administered orally.

A pharmaceutical composition according to the present invention may be comprised in a tablet, a capsule or a film-coated tablet.

In one embodiment, the pharmaceutical dosage form according to the invention has dissolution properties such that after 45 minutes at least 75%, preferably at least 80%, preferably at least 90% by weight of the pharmaceutical active ingredient is dissolved. In another embodiment after 30 minutes at least 75%, preferably at least 80%, preferably at least 90% by weight of the pharmaceutical active ingredient is dissolved. In another embodiment after 15 minutes at least 65%, preferably at least 75%, preferably at least 80%, preferably at least 90% by weight of the pharmaceutical active ingredient is dissolved. The dissolution properties can be determined in a standard dissolution test, for example as described in pharmacopoeias, such as the USP31-NF26 S2, chapter 711 (dissolution).

In one embodiment, the pharmaceutical dosage form according to the invention has disintegration properties such that within 30 minutes, alternatively within 20 minutes, preferably within 15 minutes, more preferably within 10 minutes, even more preferably within 5 minutes, the pharmaceutical dosage form is disintegrated. The disintegration properties can be determined in a standard disintegration test, for example as described in pharmacopoeias, such as the USP31-NF26 S2, chapter 701 (disintegration).

In one embodiment, the pharmaceutical dosage form according to the invention has a high content uniformity, preferably within a range from 85 to 115%, more preferably from 90 to 110%, even more preferably from 95 to 105% by weight with regard to the pharmaceutical ingredient. The content uniformity can be determined in a standard test using for example randomly 10 selected pharmaceutical dosage forms, for example as described in pharmacopoeias.

A dosage form according to this invention, such as a tablet, capsule or film-coated tablet, may be prepared by methods well-known to the one skilled in the art.

Suitable methods of manufacturing a tablet include compression of the pharmaceutical composition in the form of a powder, i.e. direct compression, or compression of the pharmaceutical composition in the form of granules, and if needed with additional excipients.

Granules of the pharmaceutical composition according to the invention may be prepared by methods well-known to the one skilled in the art. Preferred methods for the granulation of the active ingredients together with the excipients include dry granulation, also called roller compaction.

In one embodiment, the size of the granules according to the present invention is in the range from 25 to 800 μm, for example from 40 μm to 500 μm. The size of the granules may be measured via sieve analysis, for example with a sonic sifter. In one embodiment, at least 80%, at least 90%, or at least 95% by weight of the granules is in the given range.

The pharmaceutical compositions and dosage forms according to this invention may be packaged using PVC-blisters, PVDC-blisters, PVC/PVDC-blisters or a moisture-proof packaging material such as aluminium foil blister packs, alu/alu blister, transparent or opaque polymer blister with pouch, polypropylene tubes, glass bottles, PP bottles and HDPE bottles optionally containing a child-resistant feature or may be tamper evident. The primary packaging material may comprise a desiccant such as molecular sieve or silica gel to improve chemical stability of the active pharmaceutical ingredient(s). Opaque packaging such as colored blister materials, tubes, brown glass bottles or the like can be used to prolong shelf-life of the active pharmaceutical ingredient(s)I by reduction of photodegradation.

The pharmaceutical composition and the dosage forms preferably comprises one or more pharmaceutical acceptable excipients which must be "acceptable" in the sense of being compatible with the other ingredients of the formulation and not deleterious to the recipient thereof. Examples of pharmaceutically acceptable excipients are known to the one skilled in the art.

Methods for the manufacture of (E)-4-(2-(aminomethyl)-3-fluoroallyloxy)-N-tert-butylbenzamide and of salts thereof are known to the one skilled in the art. Advantageously, the compounds according to this invention can be prepared using synthetic methods as described in the literature, including patent applications as cited hereinbefore.

The active ingredient may be present in the form of a pharmaceutically acceptable salt. The phrase "pharmaceutically acceptable salt" refers to any salt preparation that is appropriate for use in a pharmaceutical application. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art and include acid addition and base salts. Hemisalts of acids and bases may also be formed. Pharmaceutically-acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, and the like).

For (E)-4-(2-(aminomethyl)-3-fluoroallyloxy)-N-tert-butylbenzamide having a basic site, suitable pharmaceutically acceptable salts may be acid addition salts. For example, suitable pharmaceutically acceptable salts of (E)-4-(2-(aminomethyl)-3-fluoroallyloxy)-N-tert-butylbenzamide may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with (E)-4-(2-(aminomethyl)-3-fluoroallyloxy)-N-tert-butylbenzamide.

S. M. Berge et al. describe pharmaceutically acceptable salts in detail in *J. Pharmaceutical Sciences*, 1977, 66:1-19. The salts can be prepared in situ during the final isolation and purification of the active ingredient, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropio-nate, phosphate, picrate, pivalate, propionate, stearate, succinate, sulfate, tartrate, thiocyanate, toluenesulfonate, undecanoate, valerate salts, and the like.

EXAMPLES AND EXPERIMENTAL DATA

The following abbreviations are used hereinbefore and hereinafter:
Ac acetyl
Et ethyl
DSC differential scanning calorimetry
h hour
HPLC high-performance liquid chromatography
MTBE methyl tert-butyl ether
r.h. relative humidity
ssNMR solid-state nuclear magnetic resonance
XRPD X-ray powder diffraction If not indicated otherwise, percent (%) values are weight/weight percent (%) values.

Preparation of Form I of (E)-4-(2-(aminomethyl)-3-fluoroallyloxy)-N-tert-butylbenzamide hydrochloride by Recrystallization (E)-4-(2-(aminomethyl)-3-fluoroallyloxy)-N-tert-butylbenzamide hydrochloride (20 g, 63.1 mmol) is suspended in isopropanol (90 ml) and heated to 82° C. Ethyl acetate (EtOAc) (80 ml) is added to the solution under reflux conditions. After the addition of seed crystals at a temperature of 75-80° C. the mixture is stirred for 5 minutes. The resulting suspension is cooled to 56° C. over a period of 1 h. Methyl tert-butyl ether (MTBE) (70 mL) is added within 5 minutes at a temperature of >50° C. The product suspension is cooled to 0-5° C., stirred for 30 minutes and filtered. The filter cake is washed with MTBE (40 ml) and the product is dried at 75° C. for about 12 h under vacuum. Form I of (E)-4-(2-(aminomethyl)-3-fluoroallyloxy)-N-tert-butylbenzamide hydrochloride is obtained as an off-white crystalline solid (18.8 g, organic purity H PLC: 99.7 area %, yield: 93.9%).

XRPD Experiments

Collection of XRPD Data

Figure 1:
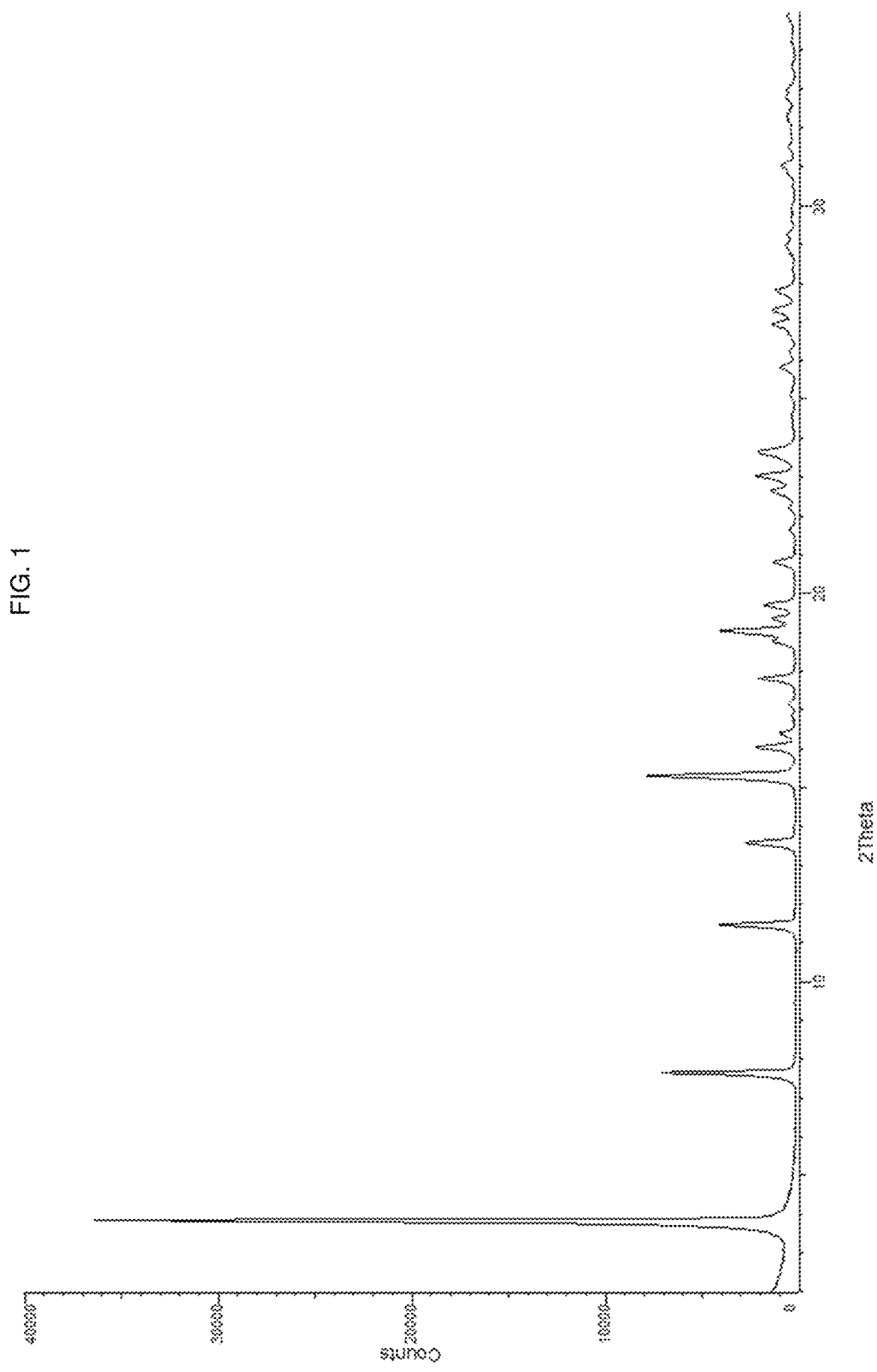
FIG. 1: XRPD pattern of Form I of (E)-4-(2-(aminomethyl)-3-fluoroallyloxy)-N-tert-butylbenzamide hydrochloride.

The X-ray powder diffraction profiles are acquired using a Bruker D8 Advance diffractometer in reflection mode equipped with a position sensitive detector using CuKα radiation (λ=1.54060 Å). For that purpose, the sample of (E)-4-(2-(aminomethyl)-3-fluoroallyloxy)-N-tert-butylbenzamide hydrochloride should be characterized by a purity above 99% as measured by HPLC, preferably the purity is above 99.5%, even more preferably above 99.7%, most preferably above 99.8%. In order to allow for experimental error, the 2θ values described herein should be considered accurate to ±0.2 degrees 2θ, in particular ±0.1 degrees 2θ, even more specifically ±0.05 degrees 2θ. That is to say, when assessing whether a given sample of crystals of (E)-4-(2-(aminomethyl)-3-fluoroallyloxy)-N-tert-butylbenzamide hydrochloride is a crystalline Form I, a 2θ value which is experimentally observed for the sample should be considered identical with a characteristic value described herein if it falls within ±0.2 degrees 2θ, in particular ±0.1 degrees 2θ, even more specifically ±0.05 degrees 2θ of the characteristic value. XRPD peaks of Form I of (E)-4-(2-(aminomethyl)-3-fluoroallyloxy)-N-tert-butylbenzamide hydrochloride are summarized in the following table. The corresponding XRPD pattern is depicted in FIG. 1.

| Peak | 2θ [°] |
|---|---|
| 1 | 3.82 |
| 2 | 7.63 |
| 3 | 11.46 |
| 4 | 13.55 |
| 5 | 15.29 |
| 6 | 16.03 |
| 7 | 16.38 |
| 8 | 17.15 |
| 9 | 17.80 |
| 10 | 18.73 |

-continued

| Peak | 2θ [°] |
|---|---|
| 11 | 19.02 |
| 12 | 19.35 |
| 13 | 19.69 |
| 14 | 20.80 |
| 15 | 21.65 |
| 16 | 22.20 |
| 17 | 22.64 |
| 18 | 23.03 |
| 19 | 23.63 |
| 20 | 24.58 |
| 21 | 25.11 |
| 22 | 25.83 |
| 23 | 26.21 |
| 24 | 26.93 |
| 25 | 27.30 |
| 26 | 27.79 |
| 27 | 28.93 |
| 28 | 29.24 |
| 29 | 31.03 |
| 30 | 31.52 |
| 31 | 32.28 |
| 32 | 32.94 |
| 33 | 33.60 |
| 34 | 34.27 |

DSC Experiments

The melting point of Form I of (E)-4-(2-(aminomethyl)-3-fluoroallyloxy)-N-tert-butylbenzamide hydrochloride is determined to be 181° C.±5° C. by DSC as onset-temperature. DSC data is acquired using a TA Instruments Q2000 DSC from 25° C. to 225° C. at a heating rate of 10° C./min. The corresponding DSC curve is depicted in FIG. 2.

EXAMPLES FOR SHELF-LIFE STABILITY TESTS

The following examples show the increased shelf-life of pharmaceutical compositions according to the present invention.

Example A: Storage Stress Tests

The content of the active ingredient, i.e. of (E)-4-(2-(aminomethyl)-3-fluoroallyloxy)-N-tert-butylbenzamide, was tested immediately after preparing the different pharmaceutical compositions ("initial" value), as well as after 1 and 2 months of storing the pharmaceutical compositions at a temperature of 60° C. in closed twist-off glass bottles. The exact list of ingredients of the different pharmaceutical compositions with and without (reference example) stabilizer are given below.

The content of the active ingredient was determined by reversed phase high performance liquid chromatography under the conditions given below.

| | Active ingredient content (% of nominal content, i.e. 1 mg as free base/tablet) | | | |
|---|---|---|---|---|
| Storage conditions | Reference example (with no acid) | Example 1 (tartaric acid) | Example 2 (fumaric acid) | Example 3 (L-glutamic acid hydrochloride) |
| Initial | 97.2 | 99.4 | 97.6 | 98.4 |
| 60° C. Closed bottle 1 month | 82.9 | 94.6 | 95.9 | 98.0 |
| 60° C. Closed bottle 2 months | Not tested | 87.8 | 95.8 | 99.4 |

Example B: Effect of Tartaric Acid on Stability

The content of the active ingredient, i.e. of (E)-4-(2-(aminomethyl)-3-fluoroallyloxy)-N-tert-butylbenzamide, was tested immediately after preparing the different pharmaceutical compositions ("initial" value), as well as after 1 and 3 months of storing the pharmaceutical compositions at different conditions in closed twist-off glass bottles. The exact list of ingredients of the different pharmaceutical compositions with different amounts of the stabilizer tartaric acid are given below.

The content of the active ingredient was determined by reversed phase high performance liquid chromatography under the conditions given below.

| | Active ingredient content (% of nominal content, i.e. 1 mg as free base/tablet) | | | | |
|---|---|---|---|---|---|
| Storage conditions | Reference example (with no acid) | Example 4 (1.3% tartaric acid) | Example 5 (2.7% tartaric acid) | Example 6 (5.3% tartaric acid) | Example 1 (10.6% tartaric acid) |
| Initial | 97.2 | 98.2 | 97.4 | 97.9 | 97.1 |
| 40° C./75% r.h. Closed bottle 1 months | 92.1 | 97.2 | 97.2 | 97.6 | 95.7 |
| 40° C./75% r.h. Closed bottle 3 months | Not tested | 96.3 | 96.3 | 97.2 | 96.4 |

Further, the effect of tartaric acid was shown by using pharmaceutical compositions with 2% tartaric acid. The content of the active ingredient, i.e. of (E)-4-(2-(aminomethyl)-3-fluoroallyloxy)-N-tert-butylbenzamide, and amount of its degradation products were tested immediately after preparing the different pharmaceutical compositions ("initial" value), as well as after 3 and 6 months of storing the pharmaceutical compositions at different conditions in closed twist-off glass bottles or aluminium blister. The exact list of ingredients of the different pharmaceutical compositions with 2% tartaric acid are given below.

The content of the active ingredient and degradation products was determined by reversed phase high performance liquid chromatography under the conditions given below. Active ingredient content (% of nominal content, top) and total amount of degradation products (%, bottom)

| Storage conditions | Example 7 (active ingredient content: 2.5 mg as free base/tablet, 2% tartaric acid) in closed bottle | Example 8 (active ingredient content: 2.5 mg as free base/tablet, 2% tartaric acid) in aluminium blister | Example 9 (active ingredient content: 5 mg as free base/tablet, 2% tartaric acid) in aluminium blister | Example 10 (active ingredient content: 1 mg as free base/tablet, 2% tartaric acid) in closed bottle |
|---|---|---|---|---|
| Initial | 97.7 | 100.0 | 99.7 | 103.9 |
|  | ≤0.1 | ≤0.1 | ≤0.1 | ≤0.1 |
| 25° C./60% r.h. 3 months | 97.1 | 99.3 | 98.6 | 104.5 |
|  | ≤0.1 | ≤0.1 | ≤0.1 | ≤0.1 |
| 25° C./60% r.h. 6 months | 96.4 | 99.8 | 99.5 | Not tested |
|  | ≤0.1 | ≤0.1 | ≤0.1 |  |
| 40° C./75% r.h. 3 months | 96.5 | 99.2 | 98.4 | 104.8 |
|  | ≤0.1 | ≤0.1 | ≤0.1 | ≤0.1 |
| 40° C./75% r.h. 6 months | 96.1 | 99.5 | 98.9 | Not tested |
|  | 0.4 | ≤0.1 | ≤0.1 |  |

Example C: Effect of L-Glutamic Acid Hydrochloride on Stability

The content of the active ingredient, i.e. of (E)-4-(2-(aminomethyl)-3-fluoroallyloxy)-N-tert-butylbenzamide, was tested immediately after preparing the different pharmaceutical compositions ("initial" value), as well as after 1 and 3 months of storing the pharmaceutical compositions at different conditions in closed twist-off glass bottles. The exact list of ingredients of the different pharmaceutical compositions with different amounts of the stabilizer L-glutamic acid hydrochloride are given below. The content of the active ingredient was determined by reversed phase high performance liquid chromatography under the conditions given below.

| Active ingredient content (% of nominal content, i.e. 1 mg as free base/tablet) | | | | | |
|---|---|---|---|---|---|
| Storage conditions | Reference example (with no acid) | Example 11 (1.3% L-glutamic acid hydrochloride) | Example 12 (2.7% L-glutamic acid hydrochloride) | Example 13 (5.3% L-glutamic acid hydrochloride) | Example 3 (10.6% L-glutamic acid hydrochloride) |
| Initial | 97.2 | 97.8 | 97.9 | 99.4 | 98.1 |
| 40° C./75% r.h. Closed bottle 1 months | 92.1 | 98.6 | 98.0 | 98.6 | 98.5 |
| 40° C./75% r.h. Closed bottle 3 months | Not tested | 99.8* | 96.5 | 99.6 | 97.2 |

*The apparent increase in the content of the active ingredient after 3 months of storage may be attributed to sample inhomogeneity and/or variablity of the HPLC method.

EXAMPLES OF FORMULATIONS

The following examples of formulations, which may be obtained analogously to methods known in the art, serve to illustrate the present invention more fully without restricting it to the contents of these examples. The term "active substance" or "active ingredient" denotes (E)-4-(2-(aminomethyl)-3-fluoroallyloxy)-N-tert-butylbenzamide or one of its pharmaceutically acceptable salts, especially (E)-4-(2-(aminomethyl)-3-fluoroallyloxy)-N-tert-butylbenzamide hydrochloride.

Reference Example: Tablet Containing 1 mg (E)-4-(2-(aminomethyl)-3-fluoroallyloxy)-N-tert-butylbenzamide (as Free Base), without Stabilizer Composition:

| (1) | (E)-4-(2-(Aminomethyl)-3-fluoroallyloxy)-N-tert-butylbenzamide hydrochloride | 1.130 mg |
|---|---|---|
| (2) | Mannitol | 82.807 mg |
| (3) | Magnesium stearate | 1.063 mg |
| | | 85.000 mg |

Preparation:

Mix (1) and (2) in an appropriate blender. Sieve the powder mixture with an appropriate sieving machine. Part of the sieved powder is premixed with (3) (ratio=1:1), then the rest of the sieved powder is added and mixed together. This mixture is compressed into 6 mm round, biconvex tablets with bevelled edges.

Example 1: Tablet Containing 1 mg (E)-4-(2-(aminomethyl)-3-fluoroallyloxy)-N-tert-butylbenzamide (as Free Base) and tartaric acid Composition:

| (1) | (E)-4-(2-(Aminomethyl)-3-fluoroallyloxy)-N-tert-butylbenzamide hydrochloride | 1.130 mg |
|---|---|---|
| (2) | Tartaric acid | 9.040 mg |
| (3) | Mannitol | 73.767 mg |
| (4) | Magnesium stearate | 1.063 mg |
| | | 85.000 mg |

Preparation:

(1) is premixed with a small amount of (3) (Active ingredient:mannitol=1:4). The premix is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 2: Tablet Containing 1 mg (E)-4-(2-(aminomethyl)-3-fluoroallyloxy)-N-tert-butylbenzamide (as Free Base) and fumaric acid Composition:

| (1) | (E)-4-(2-(Aminomethyl)-3-fluoroallyloxy)-N-tert-butylbenzamide hydrochloride | 1.130 mg |
|---|---|---|
| (2) | Fumaric acid | 9.040 mg |
| (3) | Mannitol | 73.767 mg |
| (4) | Magnesium stearate | 1.063 mg |
| | | 85.000 mg |

Preparation:

(1) is premixed with a small amount of (3) (Active ingredient:mannitol=1:4). The premix is is mixed with (2) and the rest of (3) and sieved. Part of the sieved powder is premixed with (4) (ratio=1:1), then the rest of the sieved powder is added and mixed together. This mixture is compressed into 6 mm round, biconvex tablets with bevelled edges.

Example 3: Tablet Containing 1 mg (E)-4-(2-(aminomethyl)-3-fluoroallyloxy)-N-tert-butylbenzamide (as Free Base) and L-glutamic acid hydrochloride Composition:

| (1) | (E)-4-(2-(Aminomethyl)-3-fluoroallyloxy)-N-tert-butylbenzamide hydrochloride | 1.130 mg |
|---|---|---|
| (2) | L-Glutamic acid hydrochloride | 9.040 mg |
| (3) | Mannitol | 73.767 mg |
| (4) | Magnesium stearate | 1.063 mg |
| | | 85.000 mg |

Preparation:

(1) is premixed with a small amount of (3) (Active ingredient:mannitol=1:4). The premix is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 4: Tablet Containing 1 mg (E)-4-(2-(aminomethyl)-3-fluoroallyloxy)-N-tert-butylbenzamide (as Free Base) and tartaric acid Composition:

| (1) | (E)-4-(2-(Aminomethyl)-3-fluoroallyloxy)-N-tert-butylbenzamide hydrochloride | 1.130 mg |
|---|---|---|
| (2) | Tartaric acid | 1.130 mg |
| (3) | Mannitol | 81.677 mg |
| (4) | Magnesium stearate | 1.063 mg |
| | | 85.000 mg |

Preparation:

(1) is premixed with a small amount of (3) (Active ingredient:mannitol=1:4). The premix is is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 5: Tablet Containing 1 mg (E)-4-(2-(aminomethyl)-3-fluoroallyloxy)-N-tert-butylbenzamide (as Free Base) and tartaric acid Composition:

| | | |
|---|---|---|
| (1) | (E)-4-(2-(Aminomethyl)-3-fluoroallyloxy)-N-tert-butylbenzamide hydrochloride | 1.130 mg |
| (2) | Tartaric acid | 2.260 mg |
| (3) | Mannitol | 80.547 mg |
| (4) | Magnesium stearate | 1.063 mg |
| | | 85.000 mg |

Preparation:

(1) is premixed with a small amount of (3) (Active ingredient:mannitol=1:4). The premix is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 6: Tablet Containing 1 mg (E)-4-(2-(aminomethyl)-3-fluoroallyloxy)-N-tert-butylbenzamide (as Free Base) and tartaric acid Composition:

| | | |
|---|---|---|
| (1) | (E)-4-(2-(Aminomethyl)-3-fluoroallyloxy)-N-tert-butylbenzamide hydrochloride | 1.130 mg |
| (2) | Tartaric acid | 4.522 mg |
| (3) | Mannitol | 78.285 mg |
| (4) | Magnesium stearate | 1.063 mg |
| | | 85.000 mg |

Preparation:

(1) is premixed with a small amount of (3) (Active ingredient:mannitol=1:4). The premix is is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 7: Tablet Containing 2.5 mg (E)-4-(2-(aminomethyl)-3-fluoroallyloxy)-N-tert-butylbenzamide (as Free Base) and tartaric acid Composition:

| | | |
|---|---|---|
| (1) | (E)-4-(2-(Aminomethyl)-3-fluoroallyloxy)-N-tert-butylbenzamide hydrochloride | 2.825 mg |
| (2) | Tartaric acid | 1.600 mg |
| (3) | Mannitol | 74.575 mg |
| (4) | Magnesium stearate | 0.320 mg |
| (5) | Magnesium stearate | 0.680 mg |
| (6) | Film-coating premix* | 2.500 mg |
| | | 82.500 mg |

*The film-coating premix, Opadry ® red 02F250006 INT, consists of 48% hydroxypropyl methylcellulose (HPMC), 14% polyethylene glycol (PEG), 18% titanium oxide, 18% talc and 2% iron oxide red.

Preparation:

(1) is premixed with a small amount of (3) (Active ingredient:mannitol=1:4). The premix is mixed with (2) and the rest of (3) and sieved. Part of the sieved powder is premixed with (4) (ratio=1:1), then the rest of the sieved powder is added, mixed together. This mixture is compacted by roller compactor and milled into granules. Part of the granules is premixed with (5) (ratio=1:1), then the rest of the granules is added, mixed together. This final blend is compressed into 6 mm round, biconvex tablets with bevelled edges. To prepare the coating suspension purified water is transferred to a suitable mixing vessel and (6) is added while stirring. The tablet cores are film-coated in a pan coater by spraying the coating suspension.

Example 8: Tablet Containing 2.5 mg (E)-4-(2-(aminomethyl)-3-fluoroallyloxy)-N-tert-butylbenzamide (as Free Base) and tartaric acid Composition:

| | | |
|---|---|---|
| (1) | (E)-4-(2-(Aminomethyl)-3-fluoroallyloxy)-N-tert-butylbenzamide hydrochloride | 2.825 mg |
| (2) | Tartaric acid | 1.200 mg |
| (3) | Mannitol | 55.225 mg |
| (4) | Magnesium stearate | 0.240 mg |
| (5) | Magnesium stearate | 0.510 mg |
| (6) | Film-coating premix* | 2.000 mg |
| | | 62.000 mg |

*The film-coating premix, Opadry ® red 02F250006 INT, consists of 48% hydroxypropyl methylcellulose (HPMC), 14% polyethylene glycol (PEG), 18% titanium oxide, 18% talc and 2% iron oxide red.

Preparation:

Mix (1), pre-screened (2) and (3) in an appropriate blender. Sieve the powder mixture with an appropriate sieving machine. Part of the sieved powder is premixed with (4), then the rest of the sieved powder is added, mixed together. This mixture is compacted by roller compactor and milled into granules. Part of the granules is premixed with (5), then the rest of the granules is added, mixed together. This final blend is compressed into 5.5 mm round, biconvex tablets with bevelled edges. To prepare the coating suspension purified water is transferred to a suitable mixing vessel and (6) is added while stirring. The tablet cores are film-coated in a pan coater by spraying the coating suspension.

Example 9: Tablet Containing 5.0 mg (E)-4-(2-(aminomethyl)-3-fluoroallyloxy)-N-tert-butylbenzamide (as Free Base) and tartaric acid Composition:

| | | |
|---|---|---|
| (1) | (E)-4-(2-(Aminomethyl)-3-fluoroallyloxy)-N-tert-butylbenzamide hydrochloride | 5.650 mg |
| (2) | Tartaric acid | 2.400 mg |
| (3) | Mannitol | 110.450 mg |
| (4) | Magnesium stearate | 0.480 mg |
| (5) | Magnesium stearate | 1.020 mg |
| (6) | Film-coating premix* | 4.000 mg |
| | | 124.000 mg |

*The film-coating premix, Opadry ® red 02F250006 INT, consists of 48% hydroxypropyl methylcellulose (HPMC), 14% polyethylene glycol (PEG), 18% titanium oxide, 18% talc and 2% iron oxide red.

Preparation:

Mix (1), pre-screened (2) and (3) in an appropriate blender. Sieve the powder mixture with an appropriate sieving machine. Part of the sieved powder is premixed with (4), then the rest of the sieved powder is added, mixed together. This mixture is compacted by roller compactor and milled into granules. Part of the granules is premixed with (5), then the rest of the granules is added, mixed together. This final blend is compressed into 7 mm round, biconvex tablets with bevelled edges. To prepare the coating suspension purified water is transferred to a suitable mixing vessel and (6) is added while stirring. The tablet cores are film-coated in a pan coater by spraying the coating suspension.

Example 10: Tablet Containing 1.0 mg (E)-4-(2-(aminomethyl)-3-fluoroallyloxy)-N-tert-butylbenzamide (as Free Base) and tartaric acid Composition:

| | | |
|---|---|---|
| (1) | (E)-4-(2-(Aminomethyl)-3-fluoroallyloxy)-N-tert-butylbenzamide hydrochloride | 1.130 mg |
| (2) | Tartaric acid | 0.360 mg |
| (3) | Mannitol | 16.285 mg |
| (4) | Magnesium stearate | 0.072 mg |
| (5) | Magnesium stearate | 0.153 mg |
| | | 18.000 mg |

Preparation:

Mix (1), pre-screened (2) and (3) in an appropriate blender. Sieve the powder mixture with an appropriate sieving machine. Part of the sieved powder is premixed with (4), then the rest of the sieved powder is added, mixed together. This mixture is compacted by roller compactor and milled into granules. Part of the granules is premixed with (5), then the rest of the granules is added, mixed together. This final blend is compressed into 3 mm round, biconvex tablets with bevelled edges.

Example 11: Tablet Containing 1 mg (E)-4-(2-(aminomethyl)-3-fluoroallyloxy)-N-tert-butylbenzamide (as Free Base) and L-glutamic acid hydrochloride Composition:

| | | |
|---|---|---|
| (1) | (E)-4-(2-(Aminomethyl)-3-fluoroallyloxy)-N-tert-butylbenzamide hydrochloride | 1.130 mg |
| (2) | L-Glutamic acid hydrochloride | 1.130 mg |
| (3) | Mannitol | 81.677 mg |
| (4) | Magnesium stearate | 1.063 mg |
| | | 85.000 mg |

Preparation:

(1) is premixed with a small amount of (3) (Active ingredient:mannitol=1:4). The premix is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 12: Tablet Containing 1 mg (E)-4-(2-(aminomethyl)-3-fluoroallyloxy)-N-tert-butylbenzamide (as Free Base) and L-glutamic acid hydrochloride Composition:

| | | |
|---|---|---|
| (1) | (E)-4-(2-(Aminomethyl)-3-fluoroallyloxy)-N-tert-butylbenzamide hydrochloride | 1.130 mg |
| (2) | L-Glutamic acid hydrochloride | 2.260 mg |
| (3) | Mannitol | 80.547 mg |
| (4) | Magnesium stearate | 1.063 mg |
| | | 85.000 mg |

Preparation:

(1) is premixed with a small amount of (3) (Active ingredient:mannitol=1:4). The premix is is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 13: Tablet Containing 1 mg (E)-4-(2-(aminomethyl)-3-fluoroallyloxy)-N-tert-butylbenzamide (as Free Base) and L-glutamic acid hydrochloride Composition:

| | | |
|---|---|---|
| (1) | (E)-4-(2-(Aminomethyl)-3-fluoroallyloxy)-N-tert-butylbenzamide hydrochloride | 1.130 mg |
| (2) | L-Glutamic acid hydrochloride | 4.522 mg |
| (3) | Mannitol | 78.285 mg |
| (4) | Magnesium stearate | 1.063 mg |
| | | 85.000 mg |

Preparation:

(1) is premixed with a small amount of (3) (Active ingredient:mannitol=1:4). The premix is mixed with (2) and the rest of (3) and sieved. Part of the sieved powder is premixed with (4) (ratio=1:1), then the rest of the sieved powder is added, mixed together. This mixture is compressed into 6 mm round, biconvex tablets with bevelled edges.

Example 14: Tablet Containing 5.0 mg (E)-4-(2-(aminomethyl)-3-fluoroallyloxy)-N-tert-butylbenzamide (as Free Base) and tartaric acid Composition:

| | | |
|---|---|---|
| (1) | (E)-4-(2-(Aminomethyl)-3-fluoroallyloxy)-N-tert-butylbenzamide hydrochloride | 5.65 mg |
| (2) | Tartaric acid | 1.20 mg |
| (3) | Mannitol | 52.40 mg |
| (4) | Magnesium stearate | 0.24 mg |
| (5) | Magnesium stearate | 0.51 mg |
| | | 60.00 mg |

Preparation:

(1) is premixed with a small amount of (3) (Active ingredient:mannitol=1:4). The premix is mixed with (2) and the rest of (3) and sieved. Part of the sieved powder is premixed with (4) (ratio=1:1), then the rest of the sieved powder is added, mixed together. This mixture is compacted by roller compactor and milled into granules. Part of the granules is premixed with (5) (ratio=1:1), then the rest of the granules is added, mixed together. This final blend is compressed into 5.5 mm round, biconvex tablets with bevelled edges.

Test Conditions for Reversed Phase High Performance Liquid Chromatography for the Measurements of Content of Active Ingredient Apparatus: A standard HPLC apparatus with UV detector
Column: An octylsilylated silica gel column, 3 μm, 4.6×100 mm, temperature controlled
Mobile phase: Phosphate buffer pH 4.0 and acetonitrile, gradient
Flow rate: 0.8 mL/min
Detection: UV 250 nm
Sample solvent: A 1:1 mixture of phosphate buffer pH 4.0 and acetonitrile Test Conditions for Reversed Phase High Performance Liquid Chromatography for the Measurements of Content of Active Ingredient and Degradation Products Apparatus: A standard HPLC apparatus with UV detector
Column: An octadecylsilylated silica gel column, 3 μm, 4.6×100 mm, temperature controlled
Mobile phase: Phosphate buffer pH 5.0 and acetonitrile, gradient
Flow rate: 0.8 mL/min
Detection: UV 250 nm
Sample solvent: A 1:1 mixture of phosphate buffer pH 5.0 and acetonitrile Manufacturing Process:
Manufacturing Process with Dry Granulation
Step 1.1: Mixing 1
Premix and pre-sieve (E)-4-(2-(aminomethyl)-3-fluoroallyloxy)-N-tert-butylbenzamide hydrochloride with the premixing portion of mannitol. Transfer this pre-sieved powder, along with the rest of the mannitol and stabilizer in an appropriate blender, and mix.
Step 1.2 Sieving 1
Sieve the powder mixture with an appropriate sieving machine.
Step 1.3: Mixing 2
Premix the intra-granular portion of magnesium stearate and a part of the sieved powder form step 1,2; sieve the resulting premix with a suitable sieve. Add the remaining sieved powder from step 1.2 and blend the whole mixture with an appropriate blender.
Step 2.1: Dry Granulation and Milling
Granulate the prepared mixture from step 1.3 and mill in an appropriate roller compactor.
Step 3.1: Final Blending
Premix the extra-granular portion of magnesium stearate and a part of the milled granules from step 2.1; sieve the resulting premix with a suitable sieve. Add the remaining milled granules from step 2.1 and blend the whole mixture with an appropriate blender.
Step 4.1: Tabletting
The final blend is compressed into tablets with a rotary press.
Step 5.1: Preparation of Film-Coating
The Opadry® film-coating agent is dispersed in purified water by stirring to prepare the film-coating suspension.
Step 5.2: Film-Coating
The tablets are coated with the film-coating suspension in a drum coater.

Manufacturing Process with Direct Compression
Step 1.1: Mixing 1
Premix and pre-sieve (E)-4-(2-(aminomethyl)-3-fluoroallyloxy)-N-tert-butylbenzamide hydrochloride with the premixing portion of mannitol. Transfer this pre-sieved powder, along with the rest of the mannitol and stabilizer in an appropriate blender, and mix.
Step 1.2 Sieving 1
Sieve the powder mixture with an appropriate sieving machine.
Step 1.3: Final Blending
Premix the magnesium stearate and a part of the sieved powder form step 1,2; sieve the resulting premix with a suitable sieve. Add the remaining sieved powder from step 1.2 and blend the whole mixture with an appropriate blender.
Step 2.1: Tabletting
The final blend is compressed into tablets with a rotary press.
Step 3.1: Preparation of Film-Coating
The Opadry® film-coating agent is dispersed in purified water by stirring to prepare the film-coating suspension.
Step 3.2: Film-Coating
The tablets are coated with the film-coating suspension in a drum coater.

EXAMPLES OF TREATMENTS

Example 1: Reduction of Pathologic Neoangiogenesis

The in vivo effect of the API (E)-4-(2-(aminomethyl)-3-fluoroallyloxy)-N-tert-butylbenzamide was tested after systemic administration in the oxygen-induced retinopathy (OIR) mouse model. Since the corticosteroid Dexamethasone has been shown to decrease the severity of OIR in the same model it has been included as technical control and anti-inflammatory reference compound. In this study the dose of the API was 1.8 mg/kg (as free base) and the API was employed in the form of its hydrochloride. The API and Dexamethasone were dissolved in 0.9% NaCl. The API and Dexamethasone were administered by s.c, injection. Application volume was 10 ml/kg. Control animals received vehicle only.

Neonatal mice and their mothers were exposed to 75% $O_2$ from postnatal day 7 and day 12 and returned to room temperature at P12. In this context P means postnatal day. In this model, exposure to 75% $O_2$ from P7-P12 provokes the development of a central avascular retinal region, which becomes ischemic when mice brought to room air at P12. Starting from P12, the avascular area begins to revascularize and at the same time neovascular tufts protrude towards the vitreous. At P16 and P17, aberrant pathological neovascularization peaks and revascularization is still incomplete. Mouse eyes were enucleated, fixed in 4% PFA for at least 24 h, and embedded in paraffin. Every 3rd slide from serial sections (6 μm thick) was taken from around the region of the optic nerve. The PAS-stained sections were examined for the presence of neovascular tufts projecting into the vitreous from the inner limiting membrane of the retina. The neovascular score was defined as the mean number of neovascular cell nuclei per section found in ten sections (five on each side of the optic nerve) per eye. Tufts adjacent to the optic nerve (up to 90 μm from each side) were discriminated from counting. Data are represented as mean of 10 slides ±SEM counted tuft cells with one-way ANOVA testing and $p<0.05$ regarded as significant. Treatment of neonatal mice with 1.8 mg/kg API in two consecutive s.c. injections at P12 and P14 significantly reduced retinal tuft formation by 49%

Figure 3:
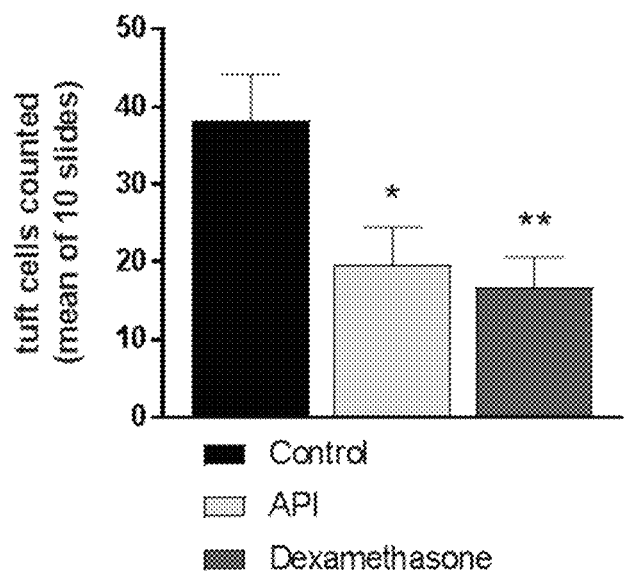
FIG. 3: Neovascular tuft formation in an oxygen-induced retinopathy mouse model with administration of (E)-4-(2-(aminomethyl)-3-fluoroallyloxy)-N-tert-butylbenzamide (API) or of dexamethosone or without administration (control).

(p<0.05) at the end of the 4 days ischemic period (P16)—see FIG. 3. The effect size was comparable to the technical control Dexamethasone (1.8 mg/kg, s.c.) which reduced the tuft number by 57% (p<0.01). In the FIG. 3 the data represent mean tuft number ±SEM with n=12-15 eyes, *, p<0.05, ** p<0.01 (ANOVA). API achieved full target engagement based on 88% inhibition of AOC3 activity in homogenates of sentinel lung tissue homogenates whereas Dexamethasone showed no significant effect.

Animals treated with the API during ischemia showed significant reduced neovascular tuft nuclei compared to the respective vehicle controls. This indicates that the API reduces pathological neovascularization and thus prevents or reduces proliferative retinopathy and a progression from NPDR to PDR.

Example 2: Protection of Retinal Function

The effects of the API (E)-4-(2-(aminomethyl)-3-fluoroallyloxy)-N-tert-butylbenzamide on the protection of retinal function were investigated in the STZ-induced diabetic rat model which is characterized by a progressive hyperglycemia-dependent neuronal dysfunction in the retina.

Figure 4:
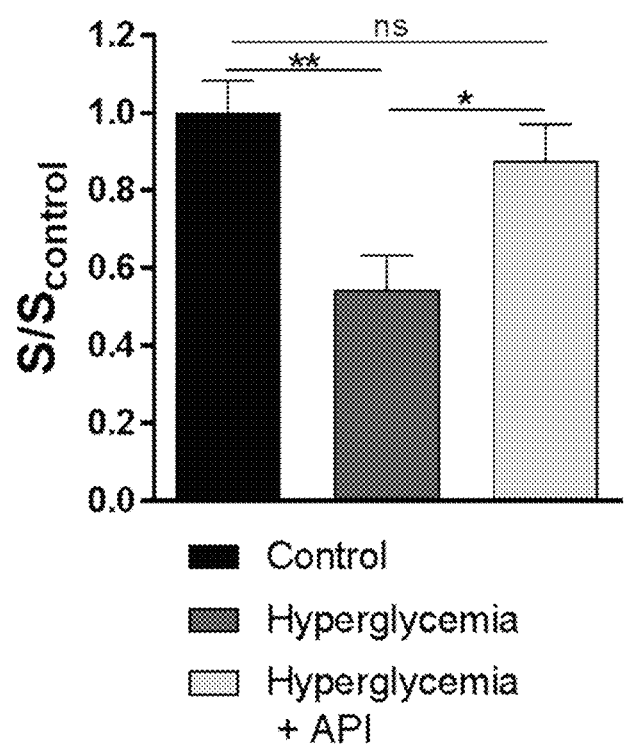
FIG. 4: Normalized light sensitivities (S/S$_{control}$) measured in control and hyperglycemic STZ-induced diabetic rats with and without administration of (E)-4-(2-(aminomethyl)-3-fluoroallyloxy)-N-tert-butylbenzamide (API).

Male Brown Norway rats (BN rats) were obtained from Charles River (Germany). Hyperglycemia was induced by i.p. injections of STZ (65 mg/kg body weight). Animals were dosed twice daily by oral application of vehicle (Natrosol), or API (1.8 mg/kg (as free base) body weight) for 5 weeks which was sufficient to achieve full target engagement, i.e. almost complete inhibition of AOC3 activity, both in the eye as well as in plasma. API was used in the form of its hydrochloride. Retinal function was assessed via electroretinography (ERG) recordings. ERG is a non-invasive electrophysiological technique to assess light-induced electrical activity of different retinal neurons, and allows for quantifying different aspects of retinal function such as dim light or color vision. After induction of diabetes via i.p. STZ application (day 1), diabetic (hyperglycemic) animals were randomized into groups of similar blood glucose concentrations (>20 mM at day 5). At week 5 post diabetes induction, ERG recordings were performed to quantify the extent of neuronal dysfunction in the retina. One diabetic group (Group 3; n=10 animals) received oral treatment with API, the non-diabetic control (Group 1; n=10 animals) and diabetic control group (Group 2; n=10 animals) received oral treatment with vehicle. The light sensitivity of rod-driven ERG b-wave responses is a measure for the number of neurons participating in the rod-driven retinal pathway (in particular photoreceptors and downstream bipolar cells), and their sensitivity towards light stimuli in order to produce depolarizing light responses. Light sensitivities S (defined as the ratio of the saturating b-wave response amplitude and the semi-saturating flash intensity) were normalized to the mean light sensitivity of nondiabetic control rats ($S_{control}$) and plotted in FIG. 4 (data are mean+SEM, eyes investigated per group: n=19 (Group 1), n=19 (Group 2), n=20 (Group 3); ns, not significant; *, p<0.05; , p<0.01; *, p<0.001 one-way ANOVA with Tukey's multiple comparisons test). Normalized light sensitivities were decreased about 40-50% in the STZ-induced hyperglycemic animals (group 2 in FIG. 4) compared to control rats (group 1). Treatment with API could significantly prevent the loss of light sensitivity, causing an increase in light sensitivity by ~30% (group 3 compared to group 2 in FIG. 4). Therefore treatment with the API protected the diabetic animals from a loss of light sensitivity of the rod-driven retinal pathway as observed in the diabetic control group. In conclusion, the results of this study provide evidence for neuroprotective effects of the API under the condition of hyperglycemic stress in the retina and thus indicate the therapeutic potential of the API in the treatment of diabetic retinopathy.

Example 3: Treatment of Diabetic Retinopathy

The impact of the API (E)-4-(2-(aminomethyl)-3-fluoroallyloxy)-N-tert-butylbenzamide, e.g. in the form of its hydrochloride, on the non-proliferative diabetic retinopathy (NPDR), in particular in the improvement of retinal lesions, in patients is investigated as follows:

Patients with NPDR, in particular moderately severe or severe NPDR, such as DRSS (diabetic retinopathy severity scale) level 47 or DRSS level 53, are treated over a period of time (e.g. for approximately 12 weeks for each patient) with the API (E)-4-(2-(aminomethyl)-3-fluoroallyloxy)-N-tert-butylbenzamide, in the form of its hydrochloride, and compared with patients who have been treated with a placebo. The patients are adult humans, preferably of age 18 years or older.

The API is administered orally once daily (for example an amount corresponding to 10 mg (E)-4-(2-(aminomethyl)-3-fluoroallyloxy)-N-tert-butylbenzamide). For example two 5 mg tablets of the pharmaceutical composition according to the Example 11 of the Section Examples of Formulations are administered orally once daily to the patient.

The patients preferably do not show diabetic macular edema, in particular center-involved diabetic macular edema (CI-DME), especially these patients do not show a central subfield thickness above 300 micrometers, e.g. measured by optical coherence tomography (OCT).

Patients are included in the study who are diagnosed of having diabetes mellitus (type 1 or type 2), preferably patients with HbA1c equal or below 10%, e.g. documented by ADA or WHO criteria, and are treated with suitable antidiabetic medication.

During (e.g. weeks 4 and 8) and at the end of a defined period of time (e.g. week 12), and during a follow-up period, the following parameters are investigated in the patients treated with API (e.g. 10 mg once daily) and in the patients with placebo:
Improvement of retinal lesions,
Proportion of patients with any ocular adverse events (according to Common Terminology Criteria for Adverse Events (CTCAE)
Proportion of patients with at least 2 steps improvement in the study eye on the DRSS,
Proportion of patients with 1 step improvement in the study eye on the DRSS,
Improvement on the individual components of the DRSS level in the study eye (retinal hemorrhages, venous beading, intraretinal microvascular abnormalities (IRMA)),
Proportion of patients with progression of disease assessed by increase in DRSS level,
Proportion of patients with at least 3 steps improvement at the patient level on the DRSS,
Change from baseline in area of non-perfusion [%] measured by widefield fluorescein angiography,
Mean change from baseline in best corrected visual acuity (BCVA),
Mean change from baseline in contrast sensitivity [number of letters],
Changes in area of non-perfusion as measured by optical coherence tomography angiogram (OCT-A).

The invention claimed is:

1. A pharmaceutical composition comprising a pharmaceutically acceptable salt of (E)-4-(2-(aminomethyl)-3-fluoroallyloxy)-N-tert-butylbenzamide having the following chemical structure

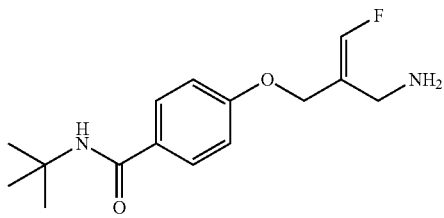 [SMILES: CC(C)(C)NC(=O)c1ccc(OC/C(=C/F)CN)cc1]

as active pharmaceutical ingredient, and one or more stabilizers selected from the group consisting of a dicarboxylic organic acid.

2. The pharmaceutical composition according to claim 1, wherein the active ingredient is (E)-4-(2-(aminomethyl)-3-fluoroallyloxy)-N-tert-butylbenzamide hydrochloride.

3. The pharmaceutical composition according to claim 1, wherein the stabilizer is selected from the group selected from the group consisting of L-glutamic acid hydrochloride, fumaric acid and tartaric acid.

4. The pharmaceutical composition according to claim 1, wherein the stabilizer is L-glutamic acid hydrochloride.

5. The pharmaceutical composition according to claim 1, wherein the stabilizer is tartaric acid.

6. The pharmaceutical composition according to claim 1, wherein the active ingredient represents 25% or less of the weight of the pharmaceutical composition.

7. The pharmaceutical composition according to claim 1, wherein the stabilizer represents 0.5% to 20% by weight of said composition.

8. The pharmaceutical composition according to claim 1, wherein said composition comprises:

|  | Amount (% by weight) |
| --- | --- |
| Active ingredient | 0.5-25 |
| One or more stabilizers | 0.5-15 |
| One or more diluents | 60-98.5 |
| optionally one or more additional additives. | ad 100% |

9. The composition according to claim 1, further comprising one or more lubricants.

10. A pharmaceutical dosage form comprising a pharmaceutical composition according to claim 1.

11. The pharmaceutical dosage form according to claim 10, wherein said dosage form is a tablet.

12. The pharmaceutical dosage form according to claim 11, further comprising one or more film coats.

13. The pharmaceutical dosage form according to claim 10, wherein the dose of the active substance is from 1 to 10 mg of (E)-4-(2-(aminomethyl)-3-fluoroallyloxy)-N-tert-butylbenzamide per tablet.

* * * * *